(12) United States Patent
Ferrand-Drake del Castillo et al.

(10) Patent No.: US 12,383,490 B2
(45) Date of Patent: Aug. 12, 2025

(54) GENERIC HIGH-CAPACITY PROTEIN CAPTURE AND TUNABLE ELECTROCHEMICAL RELEASE

(71) Applicant: Nyctea Technologies AB, Mölndal (SE)

(72) Inventors: Gustav Ferrand-Drake del Castillo, Gothenburg (SE); Andreas Dahlin, Västra Frölunda (SE)

(73) Assignee: Nyctea Technologies AB, Mölndal (SE)

( * ) Notice: Subject to any disclaimer, the term of this patent is extended or adjusted under 35 U.S.C. 154(b) by 620 days.

(21) Appl. No.: 17/756,253

(22) PCT Filed: Nov. 19, 2020

(86) PCT No.: PCT/SE2020/051106
§ 371 (c)(1),
(2) Date: May 19, 2022

(87) PCT Pub. No.: WO2021/107836
PCT Pub. Date: Jun. 3, 2021

(65) Prior Publication Data
US 2022/0409726 A1  Dec. 29, 2022

(30) Foreign Application Priority Data
Nov. 26, 2019 (SE) .................................. 1951349-8

(51) Int. Cl.
| | | |
|---|---|---|
| *A61K 9/00* | (2006.01) |
| *B81C 1/00* | (2006.01) |
| *C08F 292/00* | (2006.01) |
| *G01N 33/68* | (2006.01) |

(52) U.S. Cl.
CPC ........ *A61K 9/0009* (2013.01); *B81C 1/00206* (2013.01); *C08F 292/00* (2013.01); *C08F 2438/01* (2013.01); *G01N 33/6803* (2013.01)

(58) Field of Classification Search
None
See application file for complete search history.

(56) References Cited

U.S. PATENT DOCUMENTS 6,132,752 A * 10/2000 Pickett .................. A61N 1/0436
424/449
2012/0164749 A1  6/2012 Luchini et al.

FOREIGN PATENT DOCUMENTS

| CN | 101813701 A | 8/2010 |
| CN | 102295720 A | 12/2011 |
| CN | 103998932 A | 8/2014 |
| CN | 109239159 A | 1/2019 |
| TW | 200538556 A | 12/2005 |

OTHER PUBLICATIONS

Mallawarachchi, S. et al., "Mechanics of controlled release of insulin entrapped in polyacrylic acid gels via variable electrical stimuli," Drug Delivery and Translational Research, vol. 9, 783-794 (2019).*
Smutok, O. et al., "Recent insights in electrochemically induced pH-change system triggering payload release for biomedical application," Current Opinion in Electrochemistry, vol. 39, pp. 1-7 (2023).*
Anselmo, Aaron, et al., "Non-invasive delivery strategies for biologics", Natural Reviews Drug Discovery, vol. 18, No., (2019), pp. 19-40. Doi:10.1038/nrd.2018.183.
Baker, Gregory, et al., "Applications of Polymer Brushes in Protein Analysis and Purification", Annual Review of Analytical Chemistry, vol. 2, No., (2009), pp. 387-408.
Borisova, O.V., et al., "pH- and Electro-Responsive Properties of Poly(acrylic acid) and Poly(acrylic acid)-block-poly(acrylic acid-grad-styrene) Brushes Studied by Quartz Crystal Microbalance with Dissipation Monitoring", Langmuir, vol. 31, No., (2015), pp. 7684-7694. DOI: 10.1021/acs.langmuir.5b01993.
Dahlin, Andreas, et al., "High-Resolution Microspectroscopy of Plasmonic Nanostructures for Miniaturized Biosensing", Analytical Chemistry, vol. 81, No. 16, (2009), pp. 6572-6580.
Dai, Jinhua, et al., "High-Capacity Binding of Proteins by Poly(Acrylic Acid) Brushes and Their Derivatives", Langmuir, vol. 22, No. 9, (2006), pp. 4274-4281. 10.1021/la0600550.
Del Castillo, Gustav, et al., "Enzyme Immobilization in Polyelectrolyte Brushes: High Loading and Enhanced Activity Compared to Monolayers", Langmuir, vol. 35, No., (2009), pp. 3479-3489. DOI: 10.1021/acs.langmuir.9b00056.
Dong, Rong, et al., "Patterned Biofunctional Poly(acrylic acid) Brushes on Silicon Surfaces", Biomacromolecules, vol. 8, No., (2007), pp. 3082-3092. 10.1021/bm700493v.
Duhlin, Andreas, et al., "Sensing applications based on plasmonic nanopores: The hole story", Analyst, vol. 140, No., (2015), pp. 4748-4759. DOI: 10.1039/c4an02258k.
Farra, Robert, et al., "First-in-Human Testing of a Wirelessly Controlled Drug Delivery Microchip", Drug Delivery, vol. 4, No. 122, (2012), pp. 1-10. doi:10.1126/scitransimed.3003276.
Ferrand-Drake, Gustav, et al., "Quantitative Analysis of Thickness and pH Actuation of Weak Polyelectrolyte Brushes", The Journal of Physical Chemistry, vol. 122, No., (2018), pp. 27516-27527. Doi:10.1021/acs.jpcc.8b09171.

(Continued)

Primary Examiner — John Pak
(74) Attorney, Agent, or Firm — KNOBBE, MARTENS, OLSON & BEAR, LLP

(57) ABSTRACT

An electrochemical catch-release system (1) for repeated use comprising pH-responsive polymers (2) covalently linked to a structure (3) via a monolayer (4) of electrochemically insensitive aryl bonds, forming a polyelectrolyte arrangement (5), the polyelectrolyte arrangement (5) being arranged to, when the covalently bounded polymers (2) are in a neutral state, catch an entity (6) being a protein, a vesicle, or a compound modified with poly(ethylene glycol) by non-electrostatic interactions e.g. hydrogen bonds, and when the polymers (2) are in a charged state, release by electrostatic repulsion an entity (6) captured by the polyelectrolyte arrangement (5). The system also comprising a device (7) for applying an electrochemical potential to the polyelectrolyte arrangement (5) to induce a switch of the polyelectrolyte arrangement (5) from the neutral state to the charged state or the reverse in the presence of redox active species.

12 Claims, 18 Drawing Sheets

(56) References Cited

OTHER PUBLICATIONS

Fomina, N., et al., "An electrochemical platform for localized pH control on demand", Lab On a Chip, vol. 16, No., (2016), pp. 2236-224. DOI: 10.1039/c6lc00421k.

Gagnon, Pete, et al., "Technology trends in antibody purification", Journal of Chromatography, vol. 1221, No., (2012), pp. 57-70. dx.doi.org/10.1016/j.chroma.2011.11.003.

Gam-Derouich, Sarra, et al., "Aryl diazonium salt surface chemistry and ATRP for the preparation of molecularly imprinted polymer grafts on gold substrates", Surface and Interface Analysis, vol. 42, No., (2010), pp. 1050-1056.

Gamella, Maria, et al., "DNA Computing Systems Activated by Electrochemically-trigger DNA Release from a Polymer-brush-modified Electrode Array", Electroanalysis, vol. 28, No., (2016), pp. 1-12. dol:10.1002/elan.201600389.

Ghaly, Tammer, et al., "Electrochemical Release of Fluorescently Labeled Thiols from Patterned Gold Surfaces", Langmuir Letter, vol. 26, No. 3, (2009), pp. 1420-1423. Doi:10.1021/la9032282.

Graneli, Annette, et al., "DNA-Based Formation of a Supported, Three-Dimensional Lipid Vesicle Matrix Probed by QCM-D and SPR", Chemphyschem, vol. 5, No., (2004), pp. 729-733. DOI: 10.1002/cphc.200301061.

Gutowski, Stacie, et al., "Protease-degradable PEG-maleimide coating with on-demand release of IL-1 Ra to improve tissue response to neural electrodes", Biomaterials, vol. 44, No., (2015), pp. 55-70.

Honarvarfard, Elham, et al., "Electrochemically Stimulated Insulin Release from a Modified Graphene-functionalized Carbon Fiber Electrode", Electroanalysis, vol. 29, No. 6, (2017), pp. 1543-1553. Doi:10.1002/elan.201700095.

Huber, Dale, et al.,"Programmed Adsorption and Release of Proteins in a Microfluidic Device", Science, vol. 301, No. 5631, (2003), pp. 352-354. Doi:10.1126/science.1080759.

Katz, Evgeny, et al., "Substance Release Triggered by Biomolecular Signals in Bioelectronic Systems", The Journal of Chemical Letters, vol. 6, No., (2015), pp. 1340-1347. doi:10.1021/acs.jpclett. 5b00118.

Kayitmazer, Basak, et al., "Protein-polyelectrolyte interactions", Soft Matter, vol. 9, No., (2013), pp. 2553-2583. DOI: 10.1039/c2sm27002a.

Kusumo, Andy, et al., "High Capacity, Charge-Selective Protein Uptake by Polyelectrolyte Brushes", Langmuir, vol. 23, No. 8, (2007), pp. 4448-4454. 10.1021/la063660b.

Langer, Robert, et al., "A controlled-release microchip", Letters To Nature, vol. 397, No., (1999), pp. 335-338.

Mitragotri, Samir, et al., "Overcoming the challenges in administering biopharmaceuticals: formation and delivery strategies", Natural Reviews Drug Discovery, vol. 13, No., (2014), pp. 655-672. doi:10.1038/nrd4363.

Osada, Yoshihito, et al., "Thermal Equilibrium of the Intermacromolecular complexes of polycarboxylic acids realized by cooperative hydrogen bonding", Polymer Letters Edition, vol. 14, No., (1976), pp. 129-134.

Pinson, Jean, et al., "Attachment of organic layers to conductive or semiconductive surfaces by reduction of diazonium salts", Chemical Society Reviews, vol. 34. No., (2005), pp. 429-439. DOI: 10.1039/b406228k.

Richards, Amy, et al., "Multi-pulse drug delivery from a resorbable polymeric microchip device", Natural Materials, vol. 2, No., (2003), pp. 767-772. doi:10.1038/nmat998.

Schuwer, Nicolas, et al., "Tuning the pH Sensitivity of Poly(methacrylic acid) Brushes", Langmuir, vol. 27, No., (2011), pp. 4789-4796. dx.doi.org/10.1021/la200347u.

Shastri, Ankita, et al., "An aptamer-functionalized chemomechanically modulated biomolecule catch-and-release system", Natural Chemistry, vol. 7, No., (2015), pp. 447-454. doi:10.1038/NCHEM. 2203.

Smith, K.L., et al., Association Requirements for . . . Poly(alklene Oxides) and Polymeric Poly(carboxylic Acids), Industrial and Engineering Chemistry, vol. 51, No. 11, (1959), pp. 1361-1364.

Sun, Lei, et al., "High-Capacity, Protein-Binding Membranes Based on Polymer Brushes Grown in Porous Substrates", Chemistry Material, vol. 18, No. 17, (2006), pp. 4033-4039, 10.1021/cm060554m.

Takasu, Kenji, et al., "Polymer brush biointerfaces for highly sensitive biosensors that preserve the structure and function of immobilized proteins", Sensors and Actuators B: Chemical, vol. 216, No., (2015), pp. 428-433.

Tam, Tsz, et al., "Reversible "Closing" of an Electrode Interface Functionalized with a Polymer Brush by an Electrochemical Signal", Lamgmuir, vol. 26, No. 6, (2010), pp. 4506-4513. DOI: 10.1021/la903527p.

Wang, Fuan, et al., "Electrodissolution of Inorganic Ions/DNA Multilayer Film for Tunable DNA Release", Biomacromolecules, vol. 9, No. 10, (2008), pp. 2645-2652.

Wu, Tao, et al., "Behavior of Surface-Anchored Poly (acrylic acid) Brushes with Grafting Density Gradients on Solid Substrates: 1. Experiment", Macomolecules, vol. 40, No. 24, (2007), pp. 8756-8764. Doi: 10.1021/ma0710176.

Xiong, Kunli, et al., "Biosensing using plasmonic nanohole arrays with small, homogenous and tunable aperture diameters", Analyst, vol. 141, No., (2016), pp. 3803-3810. DOI: 10.1039/c6an00046k.

Xu, Xiao, et al., "Interaction of Proteins with Polyelectrolytes: Comparison of Theory to Experiment", Langmuir, vol. 35, No., (2019), pp. 5373-5391. DOI: 10.1021/acs.langmuir.8b01802.

Yu, et al., "Multivalent counterions diminish the lubricity of polyelectrolyte brushes", Science, vol. 360, No., (2018), pp. 1434-1438. DOI: 10.1126/science.aar5877.

Zhu, H, et al., "Catch and release cell sorting: Electrochemical desorption of T-cells from antibody-modified microelectrodes", Colloids and Surfaces B: Biointerfaces, vol. 64, No., (2008), pp. 260-268.

Xin et al., "Regulation of Protein Adsorption On pH-Responsive Surfaces", Acta Polymerica, Sinica, No. 08, Aug. 20, 2011, p. 814.

Office Action issued in Chinese patent application No. 202080081507. 8, dated Jun. 26, 2024.

Honarvarfard, Elham, et al., "Electrochemically Stimulated Insulin Release from a Modified Graphene-functionalized Carbon Fiber Electrode", Electroanalysis, vol. 29, No. 6, Mar. 3, 2017 (Mar. 3, 2017), pp. 1543-1553.

International Search Report and Written Opinion issued in corresponding PCT patent application No. PCT/SE2020/051106 on Jan. 18, 2021.

* cited by examiner

GENERIC HIGH-CAPACITY PROTEIN CAPTURE AND TUNABLE ELECTROCHEMICAL RELEASE

TECHNICAL FIELD

The present invention relates to an electrochemical catch-release system comprising pH-responsive polymers covalently linked to a structure via a monolayer of electrochemically insensitive aryl bonds forming a polyelectrolyte arrangement, and being arranged to catch and release an entity being a protein, a vesicle or a compound modified with poly(ethylene glycol) by applying an electrochemical potential to the polyelectrolyte arrangement in the presence of redox active species.

BACKGROUND

Interfaces that can capture large amounts of proteins without causing denaturation are of general interest in many areas such as purification, bioanalytics or enzymatic catalysis. The possibility to controllably release the captured proteins further opens up for new lab-on-a-chip (D. L. Huber, R. P. Manginell, M. A. Samara, B. I. Kim, B. C. Bunker, Programmed adsorption and release of proteins in a microfluidic device. Science 301, 352-354 (2003)) or drug-delivery (A. C. Anselmo, Y. Gokarn, S. Mitragotri, Non-invasive delivery strategies for biologics. Nat Rev Drug Discov 18, 19-40 (2019); E. Katz et al., Substance release triggered by biomolecular signals in bioelectronic systems. J Phys Chem Lett 6, 1340-1347 (2015); and S. Mitragotri, P. A. Burke, R. Langer, Overcoming the challenges in administering biopharmaceuticals: formulation and delivery strategies. Nat Rev Drug Discov 13, 655-672 (2014)) technologies. Several interfaces have been developed for immobilization and release of biomolecules such as DNA, (F. Wang, D. Li, G. P. Li, X. Q. Liu, S. J. Dong, Electrodissolution of inorganic ions/DNA multilayer film for tunable DNA release. Biomacromolecules 9, 2645-2652 (2008) and M. Gamella et al., DNA computing systems activated by electrochemically-triggered DNA release from a polymer-brush-modified electrode array. Electroanal 29, 398-408 (2017)) insulin, (E. Honarvarfard et al., Electrochemically stimulated insulin release from a modified graphene-functionalized carbon fiber electrode. Electroanal 29, 1543-1553 (2017)) interleukins, (S. M. Gutowski et al., Protease-degradable PEG-maleimide coating with on-demand release of IL-1 Ra to improve tissue response to neural electrodes. Biomaterials 44, 55-70 (2015)) or even whole cells (H. Zhu, J. Yan, A. Revzin, Catch and release cell sorting: Electrochemical desorption of T-cells from antibody-modified microelectrodes. Colloids and Surfaces B: Biointerfaces 64, 260-268 (2008)) by various chemical interactions. Notably, proteins (in particular antibodies) now constitute most therapeutic drugs, (A. C. Anselmo, Y. Gokarn, S. Mitragotri, Non-invasive delivery strategies for biologics. Nat Rev Drug Discov 18, 19-40 (2019); and S. Mitragotri, P. A. Burke, R. Langer, Overcoming the challenges in administering biopharmaceuticals: formulation and delivery strategies. Nat Rev Drug Discov 13, 655-672 (2014)) which calls for new methods to achieve efficient immobilization and controlled release.

However, existing capture-release designs are often not compatible with proteins because they require gentle immobilization methods to preserve structure and biological activity (K. Takasu et al., Polymer brush biointerfaces for highly sensitive biosensors that preserve the structure and function of immobilized proteins. Sensors and Actuators B: Chemical 216, 428-433 (2015)). One exception is the use of receptors to capture a particular protein, which sometimes can be combined with release by changes in the chemical environment (A. Shastri et al., An aptamer-functionalized chemo-mechanically modulated biomolecule catch-and-release system. Nature Chemistry 7, 447-454 (2015)). Unfortunately, such affinity-based methods put extreme requirements on the receptor, which must keep the target proteins securely bound while being immobilized at high density with preserved activity etc. One interesting release strategy is to store molecules in microcontainers sealed by thin membranes than can be dissolved electrochemically (A. C. R. Grayson et al., Multi-pulse drug delivery from a resorbable polymeric microchip device. Nat Mater 2, 767-772 (2003); J. T. Santini, M. J. Cima, R. Langer, A controlled-release microchip. Nature 397, 335-338 (1999); and (Farra, R. et al., First-in-human testing of a wirelessly controlled drug delivery microchip. Sci Transl Med, 4, 122:122ra21, (2012)). Although promising for many compounds, this approach has generally not been used for proteins and requires advanced microfabrication. Furthermore, existing release strategies are not tunable ("all or nothing") and limited to single use since the whole chemical construct is removed (F. Wang, D. Li, G. Li, X. Liu, S. Dong, Electrodissolution of inorganic ions/DNA multilayer film for tunable DNA release. Biomacromolecules 9, 2645-2652 (2008); and T. Ghaly, B. E. Wildt, P. C. Searson, Electrochemical release of fluorescently labeled thiols from patterned gold surfaces. Langmuir 26, 1420-1423 (2010)).

Techniques for immobilization and controlled release of proteins are highly desired for bioanalytical and biomedical applications. However, to date both immobilization methods and release technologies suffer from several limitations. It is particularly difficult to find generic concepts that preserve protein structure and release them on demand in desired quantities regardless of the environment. Thus, there is a continued need for improved techniques for immobilization and controlled release of proteins.

SUMMARY

It is an object of the present disclosure to provide an improved or at least an alternative catch-release system for catch and release of an entity such as a protein.

The invention is defined by the appended independent patent claims. Non-limiting embodiments emerge from the dependent claims, the appended drawings and the following description.

According to a first aspect there is provided an electrochemical catch-release system for repeated use comprising: pH-responsive polymers covalently linked to a structure via a monolayer of electrochemically insensitive aryl bonds, forming a polyelectrolyte arrangement, the polyelectrolyte arrangement being arranged to, when the covalently bounded polymers are in a neutral state, catch an entity being a protein, a vesicle, or a compound modified with poly(ethylene glycol), and when the polymers are in a charged state, release by electrostatic repulsion an entity captured by the polyelectrolyte arrangement, a device for applying an electrochemical potential to the polyelectrolyte arrangement to induce a switch of the polyelectrolyte arrangement from the neutral state to the charged state or the reverse in the presence of redox active species.

The electrochemical catch-release system, hence, includes systems able to perform immobilization and controlled release of the entity, as described herein, wherein the entity includes e.g. a protein, such as a water-soluble protein, a vesicle, such as a water-soluble liposome, or a compound modified with poly(ethylene glycol).

Further, the electrochemical catch-release system may be implemented in purification, bioanalytics, enzymatic catalysis and also in separation technologies and analytical devices, as well as, in technologies, and implanted devices, for controlled release of proteins such as therapeutic antibodies from implanted devices, bioelectrodes, in lab-on-a-chip, organ-on-a-chip and drug-delivery technologies.

Further, the entity, as described herein, includes intact liposomes, compounds modified with poly(ethylene glycol) biomolecular drugs, proteins useful for bioanalytical and biomedical applications, as well as, protein drugs e.g. antibodies, insulin and enzymes.

The electrochemical catch-release system comprises said pH-responsive polymers, wherein the pH-responsive polymers may be, e.g., pH-responsive polymers comprising carboxylic acid groups which have ability to dissociate protons, or to uptake protons, increasing or decreasing the pH at the interface of the electrode, respectively, the pH-responsive polymers being, for example, a poly(acrylic acid) (PAA) or a poly(methacrylic acid) (PMAA).

Further, the electrochemical catch-release system comprises said pH-responsive polymers being covalently bounded to a structure forming a polyelectrolyte arrangement. The electrochemical catch-release system of the present invention encompasses any pH-responsive polyelectrolyte arrangement, wherein the polyelectrolyte arrangement comprises, for example, a polyelectrolyte brush, film, gel or layer which is linked covalently to an electrode surface by an electrochemically insensitive aryl bond such as for instance the diazonium salt surface functionalization.

Still a further embodiment is disclosed wherein the polyelectrolyte arrangement comprises a polyelectrolyte brush, film, gel or layer which is linked covalently to an electrode surface via the monolayer of electrochemically insensitive aryl bonds, formed for instance through diazonium salt surface functionalization.

A further embodiment is disclosed wherein the polyelectrolyte arrangement comprises, or is, a polyelectrolyte brush.

Said structure of the electrochemical catch-release system, in accordance with the present invention, may be, for example, a surface, for example, a planar surfaces, or the structure is a nanohole array, or the structure, e.g. a surface, is microporous or mesoporous in size allowing a multi-scale hierarchical porous structure which would allow higher surface area and thus higher protein loading capacity.

Further, said structure may be any structure that can bind a diazonium salt, i.e. the structure may be of carbon, silicon or metals, e.g. noble metals such as Au (gold) and Pt (platinum), where the surface reacts with a diazonium salt that leads to the formation of an aromatic organic layer covalently bonded to the surface.

The pH-responsive polymers are bounded via an electrochemically insensitive bond, i.e. via an electrochemically insensitive bond comprising an aryl, to said structure.

The electrochemical catch-release system enables high-capacity (several $\mu g/cm^2$) immobilization of water-soluble proteins with their secondary structure preserved. Further, with the electrochemical catch-release system, as described herein, immobilization is mediated by non-electrostatic, multivalent hydrogen bonds from carboxylic acid groups when the polyelectrolyte brush is in its neutral, protonated state. The electrochemical catch-release system, as described herein, further enables proteins to bind in their native state.

Furthermore, the electrochemical catch-release system, as described herein, enables proteins to remain inside its polyelectrolyte arrangement even when the electrochemical catch-release system is exposed to physiological fluids.

By electrochemistry, the interfacial pH of the electrochemical catch-release system, of the present invention, can be controlled so that tunable capture and release is possible. With the electrochemical catch-release system, as described herein, it is also possible to use microscale electrodes, localized delivery and patterning. In addition to proteins, intact liposomes and compounds modified with poly(ethylene glycol) can be captured and released in the same manner with the electrochemical catch-release system, of the present invention. The electrochemical catch-release system, as described herein, is useful in analytical devices and drug delivery systems. Further, with the electrochemical catch-release system an electrode interface is disclosed being capable of non-invasive and highly efficient protein immobilization with tunable electrochemical release in biological fluids.

Moreover, it has been shown that the electrochemical catch-release system can be used to spontaneously immobilize high amounts (multilayers) of proteins in their native state by immobilization by non-electrostatic intramolecular attractive interactions e.g. hydrogen bonding, to the polymer brush when the polymer brush is in its neutral protonated state. The electrochemical catch-release system, as described herein, enables that the proteins to be irreversibly bound granted that the polymer brush stays in its neutral state with preserved structure and catalytic function. By electrochemical control and if an electrochemically stable chemical anchor i.e. via an electrochemically insensitive bond comprising an aryl, enabled with the electrochemical catch-release system, as described herein, tunable release of the captured proteins is possible. The electrochemical catch-release system also works for liposomes and compounds modified with poly(ethylene glycol).

Furthermore, the electrode interface of the electrochemical catch-release system, as described herein, can release all bound proteins by a pH change that originates from the electrochemical signal to be completely re-generated, and can be reused directly after content release without any regeneration step, even for another protein if desired.

This generic technique for capture-release of proteins now enabled by the electrochemical catch-release system will be useful in future bioanalytical or biomedical devices.

With the electrochemical catch-release system described above it has been shown a new type of high-capacity protein immobilization by non-electrostatic intramolecular attractive interactions e.g. by hydrogen bonding to polyacidic brushes in the neutral state, i.e. in the polyelectrolyte arrangement of the electrochemical catch-release system, of the present invention, and subsequent release due to electrostatic repulsion induced by electrochemical control of that increases the interfacial pH. Similarly, the switch to releasing proteins by electrostatic repulsion can also be triggered by increasing the pH of the solution to which the electrode is exposed.

The electrochemical catch-release system enables that the proteins remain bound in physiological fluids and their structure is preserved. It is also possible to decrease the interfacial pH to switch a surface of polyelectrolyte arrangement of the electrochemical catch-release system, as described herein, from repelling to protein binding. The key to successful electrochemical switching lies in the chemistry used to graft the polymers, i.e. pH-responsive polymers of the electrochemical catch-release system, as described herein, to the surface, i.e. the structure of the electrochemical catch-release system, as described herein. The switch of the polyelectrolyte brush is defined to be any pH change that changes the degree of charging of the brush. The degree of charging is determined by the brush $pK_a$ (FIG. 2) and the pH of the solution that the brush is exposed to. When the pH is below the $pK_a$ of the brush it is predominantly neutral and protonated, with a low degree of charging, and when the pH is above the $pK_a$, the brush is predominantly charged, with a high degree of charging. The switch is gradual or complete depending on how large the shift in the pH is. As shown in FIG. 2, the degree of charging is very low (<0.1) below pH 5 and very high (>0.9) above pH 7. Thus, switch of the brush by electrochemistry depends on how much the pH at the interface is displaced by the electrochemical redox reaction, which is determined by the magnitude of the applied electrochemical potential. The exact value of the $pK_a$ of the brush is subject to change, which depends on the chemical identity of the brush, and by the composition of the solution, in particular the salt concentration.

Furthermore, by adjustment of the chemical properties of the brush, or by change of the solution composition e.g. salt concentration, the $pK_a$ of the brush changes to achieve advantageous interactions with proteins that further increases protein uptake. It was shown that by tuning of the solution composition e.g. low salt composition, it was possible to achieve high-capacity immobilization of proteins even at pH 7.4. This is because the polyacidic brush is sufficiently protonated, even at pH 7.4, due to low salt concentration, to attract protein by non-electrostatic intramolecular interactions e.g. hydrogen bonding.

When a relatively small voltage window (e.g. 0 to –0.5 V) was applied to the brush electrode that was exposed to a biological liquid comprising a mixture of different proteins, e.g. serum, this lead to the release of a fraction of the immobilized proteins. The fraction of released protein have relatively low isoelectric point, pI, which are expelled due to electrostatic repulsion towards the brush. The remaining fraction of protein with a relatively high pI continue to be immobilized within the brush (structure). The repetition of this procedure enriches the brush with protein that display a relatively high isoelectric point, which could be used as a method for isoelectric separation of proteins. Subsequent release of purified high pI proteins is accomplished by the application of a larger potential window (e.g. 0 to –0.75 V) that increases the pH of the brush interface sufficiently much to release all captured protein.

Gold surfaces, i.e. the structure of the electrochemical catch-release system, as described herein, have been modified, but the method, i.e. also the electrochemical catch-release system, as described herein, is applicable to any surface, i.e. structure, as described herein, that can bind the diazonium salt. Similarly, we have used planar surfaces or nanohole arrays, i.e. both being structure, as described herein, but storage capacity can naturally be increased even more by structures with higher effective surface area, i.e. nanoporous structures, as described herein or by functionalization of porous electrically conducting materials such as but not limited to carbon, noble metal electrodes, conducting oxides. For instance, we performed polymerization of PMAA within porous carbon electrodes to achieve a static binding capacity of proteins in the range of 20 mg/cm$^3$ of electrode volume, in the range as, but not limited to the binding capacities of commercial protein purification chromatography materials. Further optimization of the electrochemical catch-release system, as described herein can be further improved by optimization of the electrode structure and porosity in combination with full utilization of the protein binding capacity of the PMAA brush. Implementation of the electrochemical catch-release system, as described herein, should be straightforward in separation technologies and analytical devices where proteins are in focus. In the long-term we envision utilizing the technology, i.e. also the electrochemical catch-release system, as described herein, for controlled release of proteins such as therapeutic antibodies from implanted devices.

The pH-responsive polymers may be bounded by means of a diazonium salt to said structure and the electrochemically insensitive bond comprises an aryl.

The pH-responsive polymer may be a polyacidic polymer comprising carboxylic acid groups, acting as carboxylic acid donors.

An even further embodiment relates to an electrochemical catch-release system, as described herein, wherein the pH-responsive polymers are, e.g. a poly(acrylic acid) (PAA) or a poly(methacrylic acid) (PMAA).

The pH-responsive polymer may be of some other type of polyelectrolyte such as but not limited to polybasic polyelectrolyte e.g. poly(diethylamino)methyl methacrylate or poly(2-vinyl pyridine). Or any other pH-responsive polyelectrolyte capable of binding an entity e.g. proteins in the neutral state by non-electrostatic intramolecular protein polyelectrolyte interactions e.g. hydrogen bonding, followed by subsequent release by electrostatic repulsion where the switch in attraction and repulsion is triggered by the application of an electrochemical signal that establishes a local pH gradient. Similarly, the switch to releasing proteins by electrostatic repulsion can also be triggered by increasing the pH of the solution to which the electrode is exposed.

The entity may be a protein, such as a water-soluble protein, a vesicle, such as a water-soluble liposome, or a compound modified with poly(ethylene glycol), and/or the entity is a drug.

The structure may be a surface, for example, a planar surface or an electrode surface, or the structure may be a porous material or a nanohole array.

The structure may comprise or be made of carbon, a noble metal, e.g. gold or platinum, a conducting oxide, stainless steel or a conducting polymer.

The conducting polymer may be e.g. polythiophene, polyethyleneimine, poly(pyrrole), poly(3,4-ethylene dioxythiophene) or poly(aniline).

In one embodiment the electrode surface is of gold.

In another embodiment the electrode surface is of platinum.

In a further embodiment the electrode surface is made of carbon.

The electrochemical catch-release system is an entity capturing system, e.g. a protein capturing system.

A further embodiment of the present invention relates to an electrochemical catch-release system, as described herein, wherein the electrochemical catch-release system is an entity releasing system, e.g. a drug releasing system.

A further embodiment of the present invention relates to an electrochemical catch-release system, as described herein, wherein the electrochemical catch-release system is an entity releasing system, e.g. a cell releasing system, i.e. cell releasing via protein releasing.

An even further embodiment of the present invention relates to an electrochemical catch-release system, as described herein, wherein the electrochemical catch-release system is miniaturized, e.g. the dimensions of the electrochemical catch-release system or device is nanoscale, microscale or mesoscale in size.

The redox active species used to induce a switch in the polyelectrolyte arrangement from the charged state of the polymers to a neutral state of the polymers, may be selected from hydroquinone, hydrogen peroxide, dopamine hydrochloride (DOPA), ascorbic acid, 4-aminophenethyl alcohol (tyrosol), 3,4-dihydroxyphenetylacetic acid (DOPAC), β-nicotinamide adenine dinucleotide, oxygen and reduced disodium salt hydrate (NADH).

The electrochemical catch-release system may further comprise enzymes bound to the polyelectrolyte arrangement in which case a non redox active species may be used to produce a redox active species by the presence of a biocatalytic reaction such as but not limited to glucose which together with dissolved oxygen produces redox active hydrogen peroxide by a biocatalytic chemical transformation in the presence of the enzyme glucose oxidase. The enzymes may be e.g. glucose oxidase which performs bioelectrocatalysis where non-redox active biological metabolites such as, but not limited to, carbohydrates e.g. glucose are locally consumed at the electrode interface resulting in local acidification. Local consumption of non-redox active species using surface bound enzymes would be used to either tune the rate of protein release or prevent release from the surface from the electrochemical catch-and-release system.

The combined thickness of the polyelectrolyte arrangement, e.g. the polyelectrolyte brush, diazonium salt and electrode may be a few hundred nanometer thick to micrometer thick. However the dimensions of the electrochemical release system could be decreased further in addition to the lateral dimension which is the thickness of the electrode. Thus, further miniatyrisation is in principle not limited for devices based on the electrochemical catch-and-release system described herein, wherein the electrochemical catch-release system is an entity capturing system, e.g. a protein capturing system. The electrochemical catch-and-release system is subject to miniatyrisation for the benefit of lower invasiveness or improved functionality if the electrochemical catch-release system is an entity releasing system, e.g. a drug releasing system or if it is a protein capturing system.

An even further embodiment relates to the local consumption of biologically occurring redox active species e.g. dopamine or serotonin by applying an electrochemical potential with the electrochemical catch-and-release system to maintain local acidification of the electrode surface in-vivo or in-vitro in a living biological system. Local consumption of naturally occurring redox species in a biological system would be used to either tune the rate of protein release or prevent release from the surface until specified on-demand from the electrochemical catch-and-release system. Similarly, with the use of biocatalysis the local pH acidification of the electrode that maintains proteins bound to the electrode can be achieved using also non-redox active species such as but not limited to glucose.

According to a second aspect there is provided a protein capturing system for sensing protein presence, for harvesting protein samples, or for some other bioanalytical purpose, comprising the electrochemical catch-release system described above.

According to a third aspect there is provided a drug releasing system i.e. drug delivery system of a protein pharmaceutical comprising the electrochemical catch-release system described above.

According to a fourth aspect there is provided a method of continuous protein repulsion by continuous application of an cyclic electrochemical signal which produces a local very high pH gradient that renders the polyelectrolyte brush highly protein repellent i.e. anti-fouling, where by removal of the continuous electrochemical signal, the polyelectrolyte brush electrode rapidly captures a sample of protein on-demand.

According to a fifth aspect there is provided a method of catching and releasing an entity being a protein, a vesicle, a compound modified with poly(ethylene glycol), and/or a drug, in a catch-release system, comprising binding pH-responsive polymers covalently to a structure via a monolayer of electrochemically insensitive aryl bonds, forming a polyelectrolyte arrangement, bringing a solution comprising said entity in contact with the polyelectrolytic arrangement when the covalently bound polymers are in a neutral state, allowing the polyelectrolytic arrangement to catch said entity by non-electrostatic interactions, and applying an electrochemical potential to the polyelectrolyte arrangement in the presence of redox active species, to induce a switch in the polyelectrolyte arrangement from the neutral state of the polymers to a charged state of the polymers, thereby releasing the entity from the polyelectrolyte arrangement by electrostatic repulsion, and possibly applying an electrochemical potential to the polyelectrolyte arrangement in the presence of redox active species, to induce a switch in the polyelectrolyte arrangement from the charged state of the polymers to a neutral state of the polymers, thereby allowing the polyelectrolytic arrangement to catch an entity by non-electrostatic interactions.

The non-electrostatic interaction may be e.g. hydrogen bonds.

BRIEF DESCRIPTION OF DRAWINGS

The invention will be described in greater detail in the following, with reference to the embodiments that are shown in the attached drawings, in which.

DETAILED DESCRIPTION

The embodiments of the invention with further developments described in the following are to be regarded only as examples and are in no way intended to limit the scope of the protection provided by the patent claims.

Figure 8A:
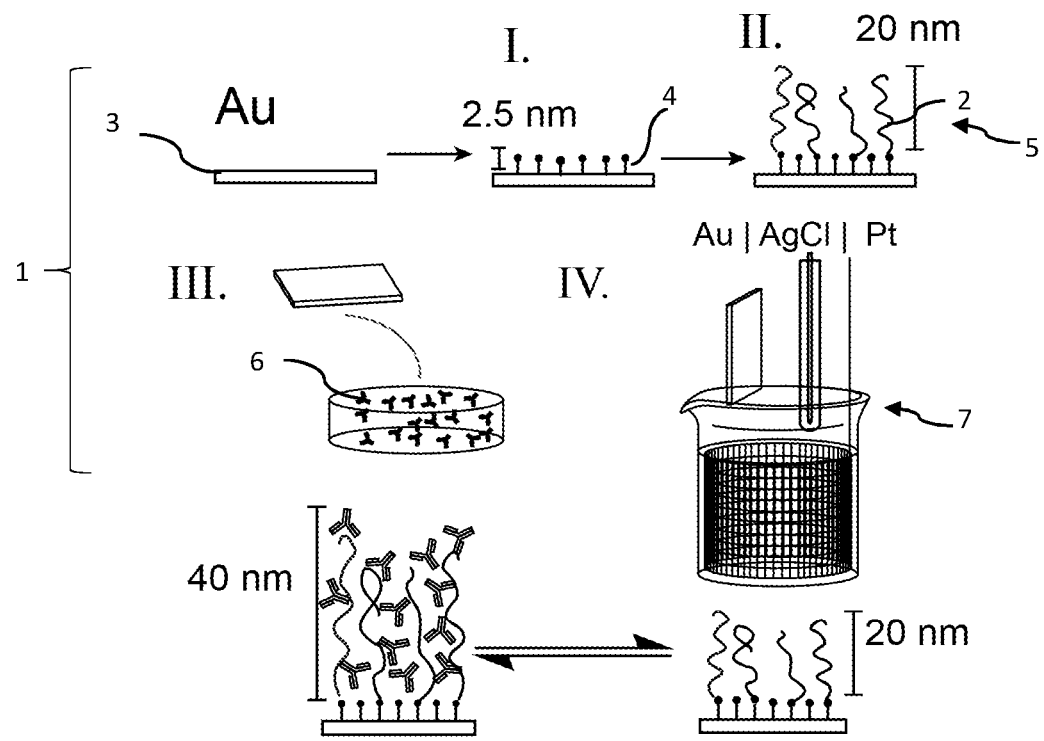
FIG. 8a shows the electrochemical catch and release system and the different steps in a method of preparing the system. Also illustrated is the use of such a system for capturing and releasing proteins.

Illustrated in FIG. 8a is an electrochemical catch-release system 1 for repeated use. The system 1 comprises pH-responsive polymers 2 covalently bounded to a structure 3 via a monolayer 4 of electrochemically insensitive aryl bonds, forming a polyelectrolyte arrangement 5. The polyelectrolyte arrangement 5 is arranged to, when the covalently bounded polymers 2 are in a neutral state, catch an entity 6 being a protein, a vesicle, or a compound modified with poly(ethylene glycol) by non-electrostatic intra-molecular bonding e.g. hydrogen bonding, and when the polymers 2 are in a charged state, release by electrostatic repulsion an entity 6 captured by the polyelectrolyte arrangement 5. A device 7 is arranged for applying an electrochemical potential to the polyelectrolyte arrangement 5 to induce a switch of the polyelectrolyte arrangement 5 from the neutral state to the charged state or the reverse in the presence of redox active species.

Below is described how such a system 1 may be manufactured and materials and chemicals needed for such manufacture. Below is also described how to use the system and examples given of difference such uses.

EXPERIMENTALS

Materials

All chemicals and proteins used were purchased from Sigma-Aldrich unless stated otherwise. $H_2O_2$ (30%) and $NH_4OH$ (28-30%) were from ACROS, while $H_2SO_4$ (98%) and ethanol (99.5%) were from SOLVECO. Water was ASTM research grade Type 1 ultrafiltered water (milli-Q-water). Chemicals used for the synthesis of diazonium salt 1 were 4-aminophenethyl alcohol, tetrafluoroboric acid (48% solution in water), acetonitrile, tert-butyl nitrate, and diethyl ether. For attaching diazonium salt to gold, L-ascorbic acid was used in water. When converting the diazonium monolayer into a polymerization initiator layer, dichloromethane, triethylamine, and α-bromoisobutyryl bromide were used. The chemicals employed in polymerization were tert-butyl acrylate, tert-butyl methacrylate, dimethylsulfoxide, dichloromethane, methane sulfonic acid, N,N,N',N''-pentamethyldiethylenetriamine (PMDTA), $CuBr_2$ and L-ascorbic acid. Buffers used in this work were based on phosphate buffered saline (PBS) tablets (0.01 M phosphate, 0.13 M NaCl, pH 7.4) or disodium hydrogen phosphate and NaCl titrated to a specific pH with HCl (1 M aqueous solution) or NaOH (1 M aqueous solution). PEG-succinimidyl Valerate (PEG-SVA, 10,000 g/mol) was used for conjugation to BSA (Laysan Bio Inc.) The lipids phosphatidylcholine and dipalmitoylphosphatidylcholine, used to prepare liposomes, were obtained from Avanti Polar Lipids. DNA samples (single-stranded and double-stranded) were available from collaborators in house. For enzyme activity assay 2,2'-azino-bis(3-ethylbenzothiazoline-6-sulphonic acid) (ABTS) and D-glucose were used.

The proteins used in this study were avidin (AVI, ThermoFisher), bovine serum albumin (BSA), BSA-fluorescein isothiocyanate conjugate, fibrinogen (FIB) from bovine plasma, glucose oxidase (GOX) Type VII G2133 from *Aspergillus niger*, horse radish peroxidase (HRP, ThermoFisher), insulin (INS), INS glargine, IgG antibodies from human serum, myoglobin (MYO) from horse skeletal muscle, lysozyme (LYS), NeutrAvidin (NAVI, Pierce), and ubiquitin (UBI) from bovine erythrocytes. Human serum (from human male AB plasma) was filtered through a 40 μm hydrophilic filter and diluted ten times in PBS prior to use. Alexa Fluor™ 488 and 555 labeling kits (ThermoFisher) were used produce different color BSA to demonstrate protein pattering. The carbohydrates used to study interactions with PMAA brushes were dextran (100,000 g/mol) from *Leuconostoc* spp., hyaluronic acid sodium salt from *Streptococcus equi* (15,000-30,000 g/mol). Oxytocin acetate salt hydrate was also tested.

The redox active species used to induce a switch in the polyelectrolyte arrangement from the charged state of the polymers to a neutral state of the polymers tested were hydroquinone, hydrogen peroxide, dopamine hydrochloride (DOPA), ascorbic acid, 4-aminophenethyl alcohol (tyrosol), 3,4-dihydroxyphenetylacetic acid (DOPAC), and β-nicotinamide adenine dinucleotide, reduced disodium salt hydrate (NADH).

Methods

Figure 14:
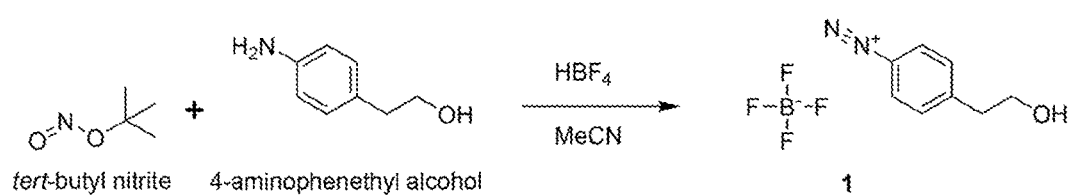
FIG. 14. shows scheme for synthesis of diazonium salt 1.

Diazonium Salt Synthesis:

The synthesis of diazonium salt (FIG. 14) involved a modified literature procedure (S. Gam-Derouich et al., Aryl diazonium salt surface chemistry and ATRP for the preparation of molecularly imprinted polymer grafts on gold substrates. Surface and Interface Analysis 42, 1050-1056 (2010)), Under an inert atmosphere, 4-aminophenethyl alcohol (2.94 g, 20 mmol) and tetrafluoroboric acid (9.94 g, 113 mmol) were dissolved in acetonitrile (20 mL). In a separate flask, tert-butyl nitrate (2.269 g, 22 mmol) was dissolved in acetonitrile (12 mL). Both solutions were degassed and cooled to −20° C. alongside 200 mL of diethyl ether. After 20 min the solutions were warmed to 0° C., before the tert-butyl nitrate solution was added to the 4-aminophenethyl alcohol solution dropwise with stirring. The reaction was then stirred for a further 1 h. The reaction was terminated by dropwise addition of the dark yellow solution to rapidly stirring diethyl ether (200 mL). After additional stirring for 1 h the supernatant was decanted off. The brown colored precipitate was dried and 3.69 g of impure diazonium salt was obtained. To verify the product, $^1$H NMR spectra were recorded at ambient temperature on a Varian 400 MHz NMR spectrometer. Spectra were analysed relative to external TMS and were referenced to the most downfield residual solvent resonance (CDCl$_3$: δH 7.26 ppm). $^1$H NMR resonances of the diazonium salt matched those previously reported (S. Gam-Derouich et al., Aryl diazonium salt surface chemistry and ATRP for the preparation of molecularly imprinted polymer grafts on gold substrates. Surface and Interface Analysis 42, 1050-1056 (2010)) and analysis revealed a purity of 80%.

Surface Cleaning:

Prior to surface functionalization, QCM sensor crystals (standard Au, purchased from Biolin Scientific) and SPR sensor surfaces (standard Au, purchased from BioNavis) were cleaned in piranha wash ($H_2SO_4$:$H_2O_2$, 3:1 v/v) for 10 min followed by rinse in milli-Q. Next, RCA1 wash ($H_2O$: $H_2O_2$:$NH_4OH$ 5:1:1 v/v at 75° C. for 20 min) was performed, followed by another rinse in milli-Q, sonication in ethanol and drying with $N_2$. For microelectrodes the piranha wash step was omitted to prevent destruction of the surface due to delamination of the porous gold film.

Figure 8B:
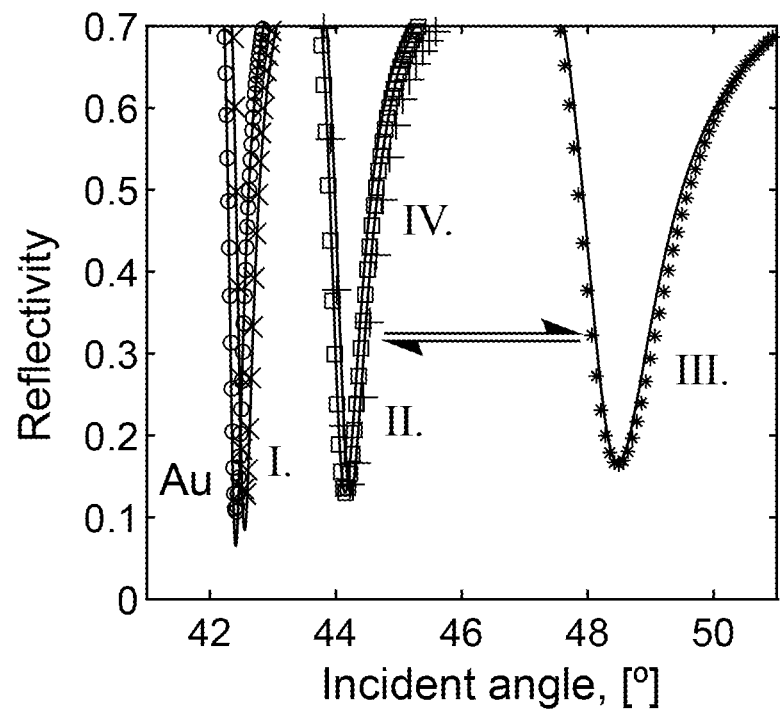
FIG. 8b shows SPR spectra during surface functionalization as well as before and after multiple cycles of immobilization and release.

Surface Activation:

Gold surfaces (QCM and SPR sensors) were placed in a glass jar with a septum seal containing diazonium salt 1 (0.301 g, 1.28 mmol) and the jar was purged with $N_2$. In a separate flask, ascorbic acid (0.028 g, 0.16 mmol) was dissolved in water (40 mL) and the solution was degassed for 1 h. Then, the ascorbic acid solution was transferred into the sealed glass jar causing dissolution of the diazonium salt. The gold surfaces were stirred in the solution for 1 h by use of a platform shaker (nitrogen bubbles that appear on the surface after 15 min indicate successful diazonium salt monolayer formation), after which they were thoroughly rinsed in water then ethanol, and dried. To convert the diazonium monolayer (the monolayer is illustrated in FIG. 8a and characterized in FIG. 8b and FIG. 15) into a polymerization initiator layer, the gold surfaces were exposed to α-bromoisobutyryl bromide (0.222 mL, 1.80 mmol) and triethylamine (0.302 mL, 2.17 mmol) in dichloromethane (20 mL) for 10 minutes, after which surfaces were rinsed in ethanol and dried under $N_2$.

Surface-Initiated Polymerization:

ATRP was used to prepare PMAA polymer brushes i.e. polyelectrolyte arrangement of the present invention, in a manner similar to published procedures (G. Ferrand-Drake del Castillo, G. Emilsson, A. Dahlin, Quantitative analysis of thickness and pH actuation of weak polyelectrolyte brushes. J Phys Chem C 122, 27516-27527 (2018)). Inhibitor was removed from the monomer tert-butyl methacrylate using an alumina column, after which it were stored at −20° C., then warmed to room temperature immediately before use. Reactions were carried out using standard Schlenk line techniques under an inert atmosphere of $N_2$. CuBr$_2$ (0.006 g, 0.03 mmol), and PMDTA (0.052 mL, 0.246 mmol) were dissolved in dimethyl sulfoxide (20 mL) and, alongside a separate flask of tert-butyl methacrylate (20 mL, 0.1231 mol), was deoxygenated via vigorous bubbling of $N_2$ for 30 min. The reaction solution and monomer were then transferred via cannula into a screw-top jar (with rubber septa lid) containing initiator-prepared gold surfaces. The reaction was initiated by the addition of ascorbic acid (0.033 g, 0.185 mmol). The final concentrations of each component in the reaction medium were: [monomer]=3.1 M, [CuBr$_2$]=0.6 mM, [PMDTA]=6.2 mM, and [ascorbic acid]=4.6 mM. The reaction was placed under magnetic stirring. Reactions were quenched by immersing the samples in pure ethanol. Poly (tert-butyl methacrylate) (PTBMA) brushes were then converted to PMAA by exposure to 0.2 mM methane sulfonic acid in dichloromethane (10 mL) for 15 min, followed by rinsing in dichloromethane and ethanol. For PAA, tert-butyl acrylate was used as the starting monomer with an otherwise identical protocol.

Porous Carbon Electrode:

A reticulated glassy carbon electrode (Redox.Me) was used as a porous electrode for evaluating possible protein purification capacity of the electrochemical catch and release system. The electrode had a bulk density of 0.05 g/cm$^3$, a porosity of 96.5% and the number of pores were 24 pores/cm with a diameter of 20 mm and 25 mm in height (7.85 cm$^3$). Surface activation and ATRP synthesis of PMAA within a porous carbon electrode was employed by scaling up the recipe by a factor 2, with equal concentrations and a total reaction volume of 80 mL. Protein immobilization tests were conducted by immersion into a BSA protein solution, 40 mg/mL set to pH 5.0, for 1 hour. The electrode was then rinsed and immersed into a beaker of PBS set to pH 8.0 to trigger release of bound protein. The static binding capacity of the electrode was evaluated by measuring the concentration of protein in the original BSA solution after electrode immersion, and the concentration of protein in the beaker to which the protein was released, The quantification of captured and released protein was measured using a NanoDrop (ThermoFisher Scientific).

Quartz Crystal Microbalance:

Sensor crystals coated with gold were used and measurements were performed using a Q-Sense E4 (Biolin Scientific). All data shown corresponds to the first or third overtone. A flow cell with an electrochemical module (QEM 401) was used to perform in-situ electrochemical experiments. A Gamry Interface 1000E potentiostat (Gamry Instruments) was connected to the electrochemical cell. For every experiment the internal resistance of the circuit was measured (Get Ru) and the open circuit potential was measured to verify an acceptable reference electrode performance and correctly connected circuit. The reference electrode used was a World Precision Instrument low leakage "Dri-ref" electrode. The scan rate in CV experiments was, unless stated otherwise, 100 mV/s.

Surface Plasmon Resonance:

Measurements were performed on a SPR Navi 220A instrument (BioNavis) both in air and water. The total internal reflection (TIR) and SPR angle was recorded on three different laser wavelengths and in two different flow channels. The flow rate of buffer used was 20 µL/min. Electrochemical SPR measurements were performed by connecting a potentiostat (same as for QCM) to a cell designed for this purpose (from the instrument manufacturer). In Fresnel modelling (G. Ferrand-Drake del Castillo, G. Emilsson, A. Dahlin, Quantitative analysis of thickness and pH actuation of weak polyelectrolyte brushes. J Phys Chem C 122, 27516-27527 (2018)), the deposited diazonium layer was assumed to have refractive index 1.5 (typical for organic coatings). The refractive index of the dry polymer brushes was assumed to be equal for PAA and PMAA and set to 1.522. The refractive index of dry proteins bound in polyelectrolyte brushes was assumed to be equal to that of the polymer. This methodology of analyzing SPR spectra and its validity has been described and demonstrated in previous work (G. Ferrand-Drake del Castillo et al., Enzyme immobilization in polyelectrolyte brushes: High loading and enhanced activity compared to monolayers. Langmuir 35, 3479-3489 (2019)). To obtain surface coverage, the densities of the dry polymers and proteins were set to 1.22 g/cm$^3$ and 1.35 g/cm$^3$, respectively.

Plasmonic Detection with Nanohole Arrays:

Microscale extinction spectroscopy was performed as described previously (A. B. Dahlin et al., High-resolution microspectroscopy of plasmonic nanostructures for miniaturized biosensing. Analytical Chemistry 81, 6572-6580 (2009)). In brief, the surface is imaged in transmission mode and a fraction of the light is directed to the opening of an optical fiber in the focal plane. The detection spot (typically 50 µm) depends on the fiber diameter and the objective magnification. The resolution is almost as high as in SPR (down to 0.1 ng/cm$^2$). Note that all data presented as resonance shifts in nm are from plasmonic nanohole arrays, while resonance shifts in degrees are from conventional angular SPR.

Fabrication of Microelectrodes:

To create microscale stripe electrodes, a laser writer (Heidelberg Instruments DWL 2000) was used. The photoresist (LOR3A) was spin coated at 4000 rpm and baked on a hotplate at 180° C. for 5 min. A second layer of S1813 was spin coated at 4000 rpm and baked on a hotplate at 120° C. for 2 min. The pattern was written by a 60 mW laser beam after which the sample was developed in developer MF-318 for 50 s. The nanohole array was then prepared by colloidal lithography. (K. Xiong, G. Emilsson, A. B. Dahlin, Biosensing using plasmonic nanohole arrays with small, homogenous and tunable aperture diameters. Analyst 141, 3803-3810 (2016)). Finally, lift-off was performed in remover RM-Rem400.

Ex-Situ Electrochemical Desorption of Proteins:

For simplicity, in some experiments protein immobilization and release was not monitored in real-time. Instead, the surfaces were immersed in a solution of proteins for 30 min to ensure saturated binding, using the kinetics from SPR and QCM measurements as guideline. Following protein loading the surface was rinsed in PBS pH 5.0 and water, and then dried with $N_2$. Desorption was performed by immersing the samples in PBS with a high pH (high enough to fully desorb the protein in question based on SPR measurements). Alternatively, electrochemical release was carried out in a beaker, with a Pt cage as counter electrode and Ag/AgCl as reference electrode. The reference electrode was prepared by depositing chloride ions onto a bare silver wire electrochemically by applying a +0.5 V for 10 min in 1 M HCl.

Fluorescence Microscopy:

All fluorescence measurements were conducted using a Zeiss Axio Observer 7 inverted microscope equipped with a Axiocam506 camera. Microelectrodes in air were imaged using a 10× objective. The background fluorescence was measured on the unfunctionalized glass surface region next to the electrodes for each dye excitation/emission filter set and subtracted from the values obtained from the electrodes.

Circular Dichroism Spectroscopy:

The polyelectrolyte brush surface was repeatedly loaded and unloaded with protein. The procedure was repeated until a sufficiently high concentration of protein was found in the collection solution. The quantification of desorbed protein was performed using a NanoDrop (ThermoFisher Scientific) . When detectable quantities of protein were obtained, the sample was filtered through a 40 µm cellulose acetate filter and placed in a centrifuge column with a molecular size cut-off of 40 kDa (Sartorius). The sample was centrifuged for 10 min at 5000 rpm resulting in approximately 100-300 µL solution with a concentration around 0.3 g/L. CD was measured with a Chirascan spectrometer (Applied Photophysics). Each spectrum is an average of 10 scans. A quartz cuvette with path length of 0.05 cm was used. Spectra of desorbed proteins were compared to corresponding protein solutions with concentration of 0.3 g/L in PBS at pH 5.0 and 8.0.

Activity Measurements:

The activity of GOX in bulk solution was measured using an ABTS and HRP assay. The reaction was initiated by the addition of GOX solution (diluted stock solution or desorbed from PMAA brush) to a mixture of ABTS, glucose and HRP in PBS pH 7.4. The final composition of the assay was 2 mM ABTS, 1 mM glucose, 20 nM HRP, and 2 nM GOX and the total volume for each measurement was 800 µL. To quantify the converted amount by GOX, a standard curve was produced where hydrogen peroxide was added instead of GOX. Absorbance was recorded at 420 nm and the initial rate was determined by determining the slope of absorbance increase during the first 30 s of the reaction.

Protein Conjugation:

PEG conjugation of BSA was performed by mixing PEG-SVA (100 mg) with BSA (5 mg) in PBS pH 8.0 for 16 h. Purification of PEG conjugated BSA from non-conjugated BSA and hydrolyzed PEG-SVA was performed by passing the reaction solution through a size exclusion column, 16/600 Superdex 200 pg, connected to an ÄKTA Start protein purification system (GE Healthcare). Analysis of protein fractions by gel electrophoresis showed a molecular weight above 250,000 kg/mol. Two different fluorophores were used in the conjugation of fluorescent dyes to the amines of BSA: Alexa Fluor 488 and 555 (with tetrafluorophenyl or N-hydroxysuccinimide ester groups). A BSA solution (100 μL, 10 mg/mL, pH 8.5) was mixed with Alexa Fluor dye (100 μg), and the resulting solution was inverted every 10 min for 1 h. The reaction was terminated by the addition of PBS pH 5.0, which reduced the pH to 5.0 and diluted the sample to a protein concentration of 0.2 mg/mL. The fluorescent proteins were immobilized in PMAA brushes in the same manner as the native proteins. GOX conjugation to PMAA brushes was performed using an EDC/NHS protocol. First the polymer brush surface was exposed to a mixture of EDC (4 mM) and NHS (2 mM) in a pH 4.0 MES buffer (20 mM) for 10 minutes. The samples were then rinsed in MES buffer and exposed to a GOX solution 0.2 (g/L) for 20 minutes. After coavelent enzyme attachment loosely bound GOX was rinsed away in MES buffer. To restore the pH-sensitivity of the brush all unreacted carboxylic acids were rehydrolysed, first by brief exposure to phosphate buffer set to pH 8.5, then by continuous exposure to phosphate buffer, pH 7.4, for at least 2 hours. The restoration of pH sensitivity after rehydrolysis of unreacted carboxylic acids following EDC/NHS was monitored using QCM-D by switching solution pH switching between pH 5 and 7.4.

Vesicle Preparation:

Vesicles were prepared by established methods (A. Graneli, M. Edvardsson, F. Hook, DNA-based formation of a supported, three-dimensional lipid vesicle matrix probed by QCM-D and SPR. Chemphyschem 5, 729-733 (2004)). In brief, the lipids were dried onto the interior of a glass vial by letting the solvent evaporate, followed by rehydration in buffer and extrusion through polycarbonate track-etched membranes with diameter of 100 nm.

EXAMPLES

Preparation of Poly(Acrylic Acid) (PAA) and Poly(Methacrylic Acid) (PMAA) Brushes by Surface-Initiated Activator-Regenerated Atom Transfer Radical Polymerization (ATRP) on Gold Surfaces, i.e. Preparation of an Electrochemical Catch-Release System, According to the Present Invention—Brush Characterization and Switching.

Figure 1:
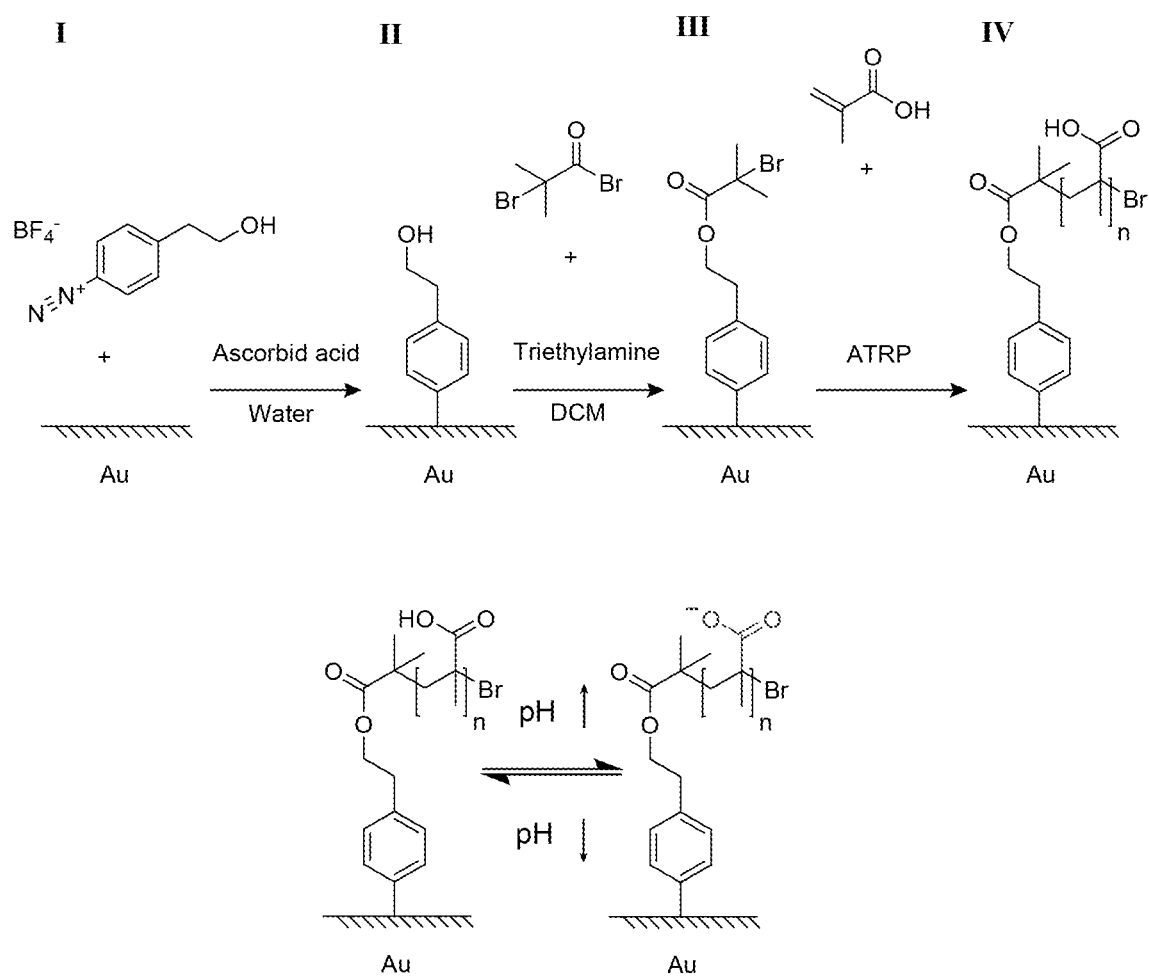
FIG. 1 shows a scheme for creating the electrochemically active and pH-responsive brush interface, i.e. of the polyelectrolyte arrangement of the electrochemical catch-release system, in accordance with the present invention.
Figure 2:
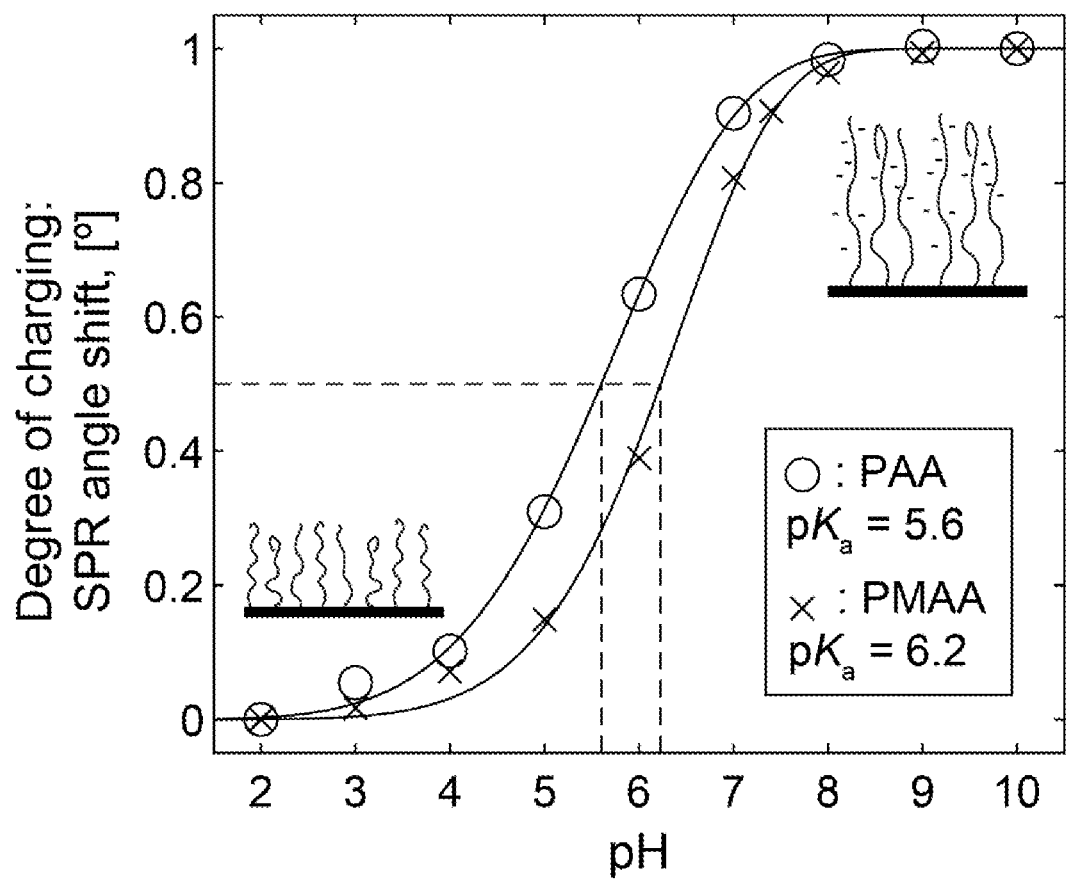
FIG. 2 shows determination of brush $pK_a$ by titration in SPR of polyelectrolyte brushes, PAA and PMAA, i.e. polyelectrolyte arrangement of the electrochemical catch-release system according to the present invention.
Figure 15:
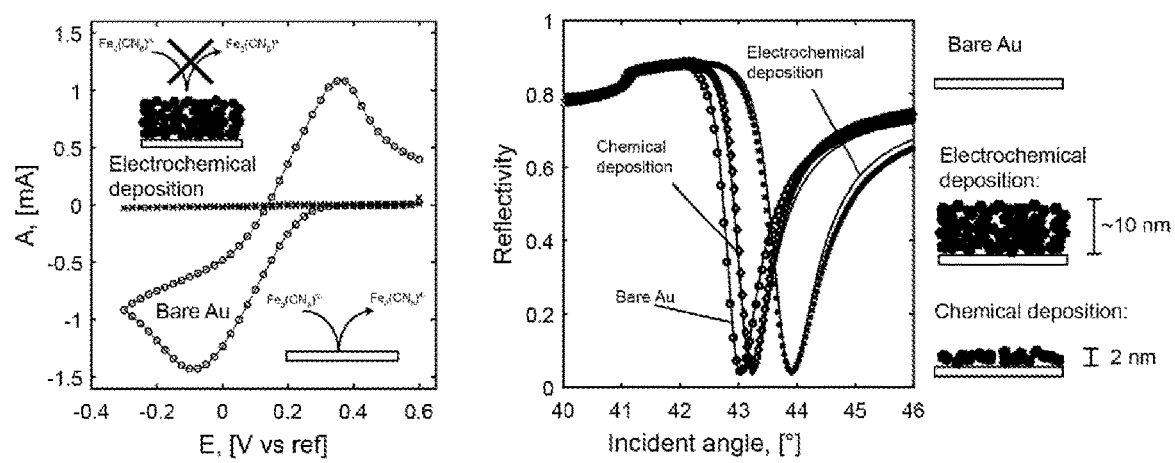
FIG. 15. shows cyclic voltagram scans of electrochemically deposited diazonium salt compared with a bare gold electrode and corresponding air scans by SPR comparing chemically deposited diazonium salt with electrochemically deposited diazonium salt. Only when diazonium salt is deposited chemically the layer is thin enough to produce Faradaic reactions meaning chemical deposition is required to achieve electrochemical switching of the polyelectrolyte brush i.e. of polyelectrolyte arrangement according to the present invention.

We prepared poly(acrylic acid) (PAA) and poly(methacrylic acid) (PMAA) brushes, i.e. polyelectrolyte arrangement of the present invention, by surface-initiated activator-regenerated atom transfer radical polymerization (ATRP) on gold surfaces, i.e. we prepared an electrochemical catch-release system, according to the present invention. A diazonium salt (S. Gam-Derouich et al., Aryl diazonium salt surface chemistry and ATRP for the preparation of molecularly imprinted polymer grafts on gold substrates. Surf Interface Anal 42, 1050-1056 (2010)) was synthesized (FIG. 14) and reduced by ascorbic acid to generate an aryl monolayer covalently linked to gold (FIG. 1, FIG. 15). The monolayer was converted to ATRP initiator layer, after which the polymerization was performed (FIG. 1). The weak polyacidic brushes, i.e. an electrochemical catch-release system, according to the present invention, had dry thicknesses in the range of tens of nm as determined by surface plasmon resonance (SPR) (G. Ferrand-Drake del Castillo, G. Emilsson, A. Dahlin, Quantitative analysis of thickness and pH actuation of weak polyelectrolyte brushes. J Phys Chem C 122, 27516-27527 (2018)). The effective $pK_a$ of the brushes, i.e. an electrochemical catch-release system, according to the present invention, was analyzed by titration in SPR (FIG. 2). As we have previously shown (G. Ferrand-Drake del Castillo, G. Emilsson, A. Dahlin, Quantitative analysis of thickness and pH actuation of weak polyelectrolyte brushes. J Phys Chem C 122, 27516-27527 (2018)), this yields results identical to those obtained from analysis by infrared spectroscopy (G. Ferrand-Drake del Castillo, G. Emilsson, A. Dahlin, Quantitative analysis of thickness and pH actuation of weak polyelectrolyte brushes. J Phys Chem C 122, 27516-27527 (2018)). Note that the high $pK_a$ values of the polyacidic brushes, i.e. an electrochemical catch-release system, according to the present invention, (compared to the same molecules in solution) are expected (T. Wu et al., Behavior of surface-anchored poly(acrylic acid) brushes with grafting density gradients on solid substrates: 1. Experiment. Macromolecules 40, 8756-8764 (2007); and N. Schuwer, H. A. Klok, Tuning the pH sensitivity of poly(methacrylic acid) brushes. Langmuir 27, 4789-4796 (2011)) and so is the higher $pK_a$ for PMAA compared to PAA (G. Ferrand-Drake del Castillo, G. Emilsson, A. Dahlin, Quantitative analysis of thickness and pH actuation of weak polyelectrolyte brushes. J Phys Chem C 122, 27516-27527 (2018)).

We found that our surface functionalization protocol (illustrated in FIG. 15) provided a polymer anchor which was stable during electrochemical potential sweeps, while still allowing Faradaic reactions. Furthermore, the brushes, i.e. polyelectrolyte arrangement of the present invention, were electro-responsive to reductive potentials because this increases the local pH by consumption of protons and oxygen:

$$O_2 + 4H^+ + 4e^- \rightarrow 2H_2O \quad (1),$$

$$O_2 + 2H^+ + 2e^- \rightarrow H_2O_2 \quad (2),$$

$$H_2O_2 + 2H^+ + 2e^- \rightarrow 2H_2O \quad (3)$$

(T. K. Tam et al., Reversible "closing" of an electrode interface functionalized with a polymer brush by an electrochemical signal. Langmuir 26, 4506-4513 (2010)).

Figure 3:
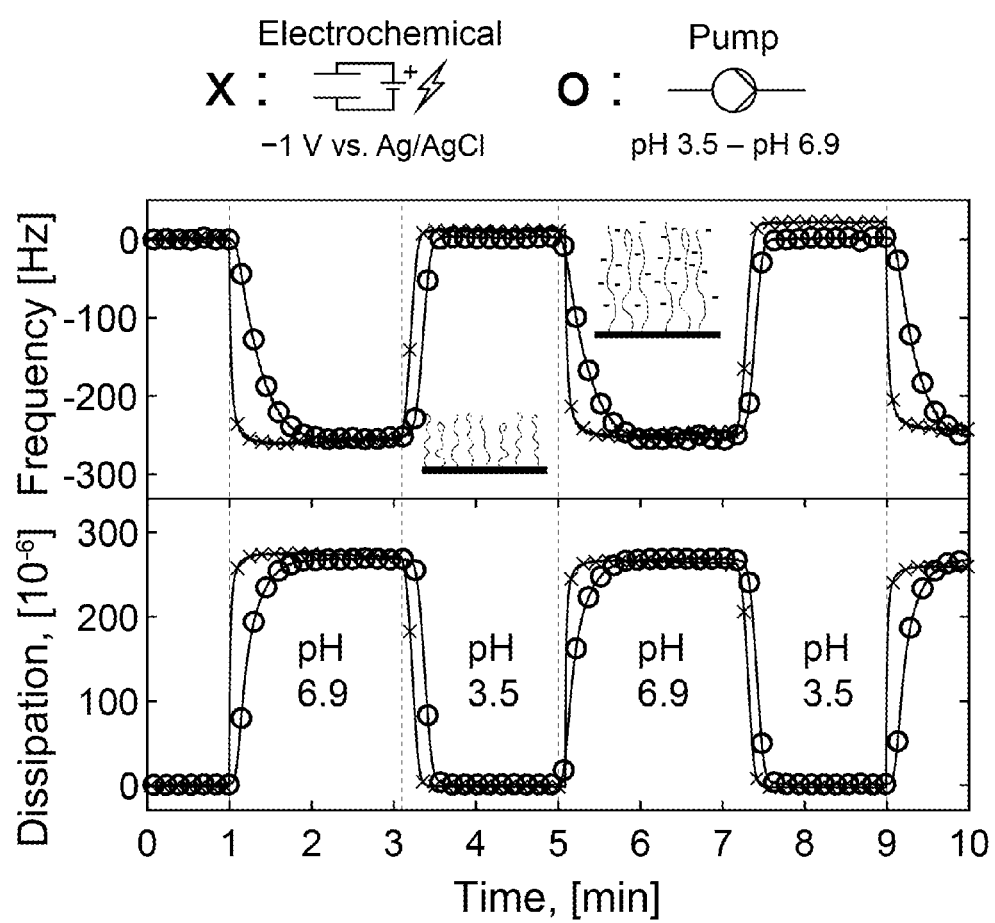
FIG. 3 shows electrochemical polyacidic brush switching monitored in QCM i.e. of polyelectrolyte arrangement of the electrochemical catch-release system according to the present invention. The response from changing the buffer pH is also shown for comparison.

Electrochemical quartz crystal microbalance (0. V. Borisova, L. Billon, R. P. Richter, E. Reimhult, O. V. Borisov, pH- and electro-responsive properties of poly(acrylic acid) and poly(acrylic acid)-block-poly(acrylic acid-grad-styrene) brushes studied by quartz crystal microbalance with dissipation monitoring. Langmuir 31, 7684-7694 (2015)) (QCM) data showed that the brushes, i.e. an electrochemical catch-release system, according to the present invention, could be fully switched to their charged state by potential control, i.e. the response was the same as when flowing buffers that had pH well above and below the brush $pK_a$ (FIGS. 2 and 3). This means that by application of an electrochemical potential the interface pH can be displaced to move between a fully charged state, all monomers of the polyelectrolytes within the brush are charged, to a completely neutral state where all monomers are neutral and protonated. By applying a weaker electrochemical signal the produced pH gradient is lower in magnitude, which leads to partial charging of the brush proportional to the degree of charging as a function of pH shown in FIG. 2. The switching was very fast (<1 s) even in a buffered environment and there was no indication of polymer desorption. We attribute this to the highly accessible electrode surface underneath the brush, i.e. an electrochemical catch-release system, according to the present invention, and the electrochemically insensitive aryl-gold bond. As expected, thiol-based anchoring resulted in polymer desorption at negative potentials (T. Ghaly, B. E. Wildt, P. C. Searson, Electrochemical release of fluorescently labeled thiols from patterned gold surfaces. Langmuir 26, 1420-1423 (2010)) and electrografted aryl diazonium layers blocked electron transfer (J. Pinson, F. Podvorica, Attachment of organic layers to conductive or semiconductive surfaces by reduction of diazonium salts. Chemical Society Reviews 34, 429-439 (2005)) (FIG. 15). The brushes were significantly harder to switch in buffers purged with nitrogen, which confirms that the effect originates from omnipresent 02 in aqueous solutions (~0.3 mM at NTP). We observed no influence from the liquid flow rate on the switching capability.

Figure 12:
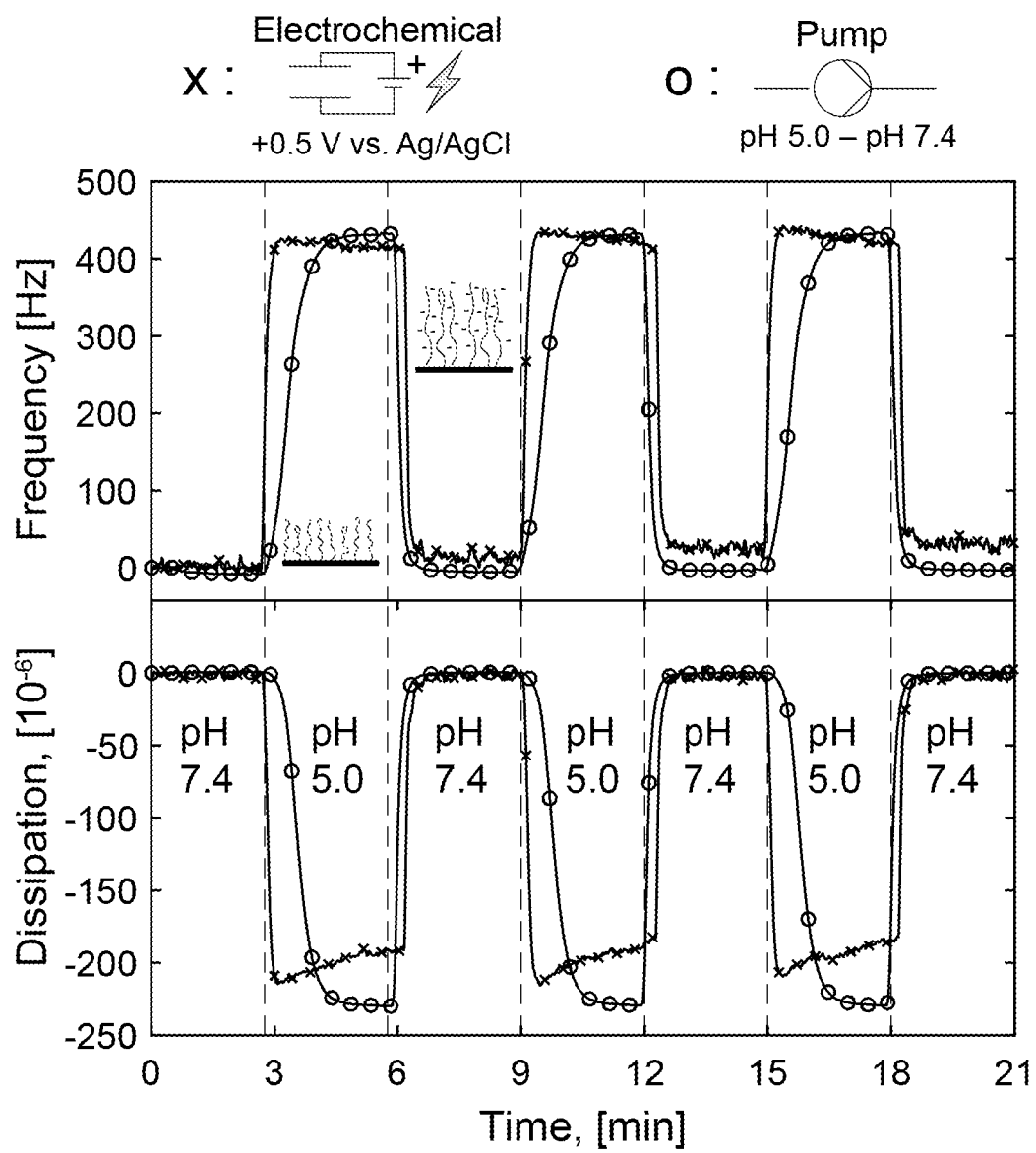
FIG. 12 shows electrochemical QCM showing brush collapse due to electrochemically induced acidification. The response when changing buffers by pumping is shown for comparison.

By application of negative potentials in acidic pH solutions we were able to show local increase of the pH at the electrode interface. However we also accomplished polyelectrolyte brush switches from charged to neutral by application of a positive potential in the presence of redox species which generate protons producing a locally acidified interface. For instance, in FIG. 12 electrochemically induced collapse of the polyelectrolyte brush was achieved when a positive potential (+0.5 V) was applied in the presence of 5 mM hydroquinone (HQ) which produces a locally increased proton concentration (decrease in pH) according to Eq. 3. (N. Fomina et al., An electrochemical platform for localized pH control on demand. Lab Chip 16, 2236-2244 (2016)).

$$HQ \rightarrow H^+ + Q^- \quad (3)$$

A local reduction of pH was produced with multiple different redox species, we even found that biologically occurring molecules e.g. Dopamine could switch the brush, but hydroquinone most readily reacted to produce a rapid acidification.

A biological environment typically does not contain a high enough concentration of quinones or redox active neurotransmitting substances to be useful in switching the brush electrochemically in vivo. To expand the usefulness of the catch and release system also in buffered neutral pH environments we investigated alternative routes for obtaining electrochemical switches of the PMAA brush that utilized abundant naturally occurring substances. Furthermore, we also investigated the possibility of using other electrode supports than gold, which may expand the range of electrochemical reactions which can occur on the surface and possibly also reduce the potential window needed to achieve electrochemical switching.

Figure 19:
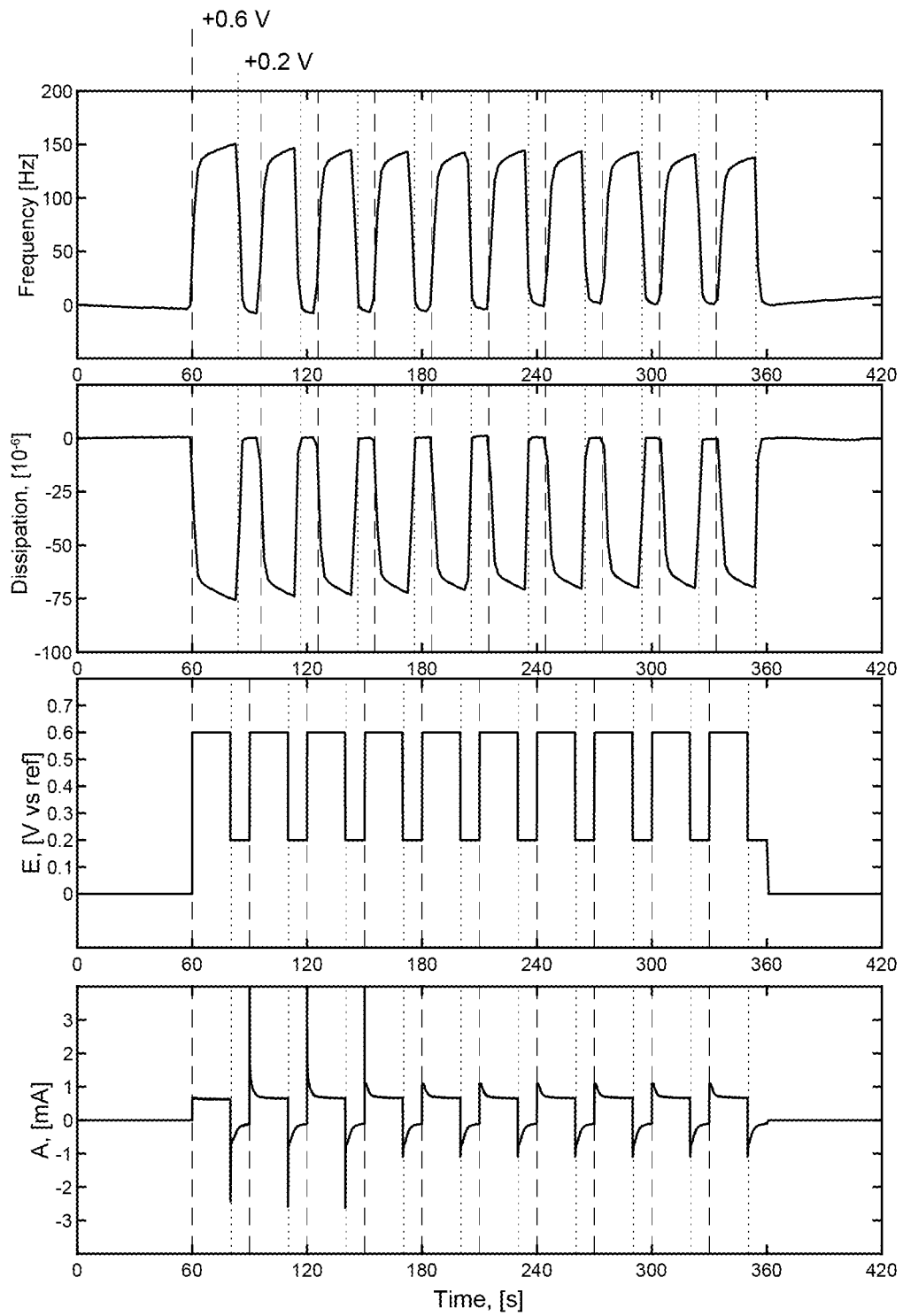
FIG. 19 shows an in-situ electrochemical QCM experiment where hydrogen peroxide is used to switch PMAA brushes functionalized on platinum surfaces, as shown in the frequency and dissipation signals the brush rapidly switches by alternating chronoamperometric application of potentials +0.6 V and +0.2 V shown in (C) together with the corresponding current recording as a function of time shown in (D).

When platinum was used instead of gold as the underlying electrode surface, this resulted in altered electrochemical properties. Platinum electrodes required lower magnitude of potentials (+/−10 mV) to switch the brush pH. In addition the electrochemical properties of platinum made it possible to perform more electrochemical reactions, for instance, hydrogen peroxide could be utilized as a redox species. For instance, by using a platinum surface we could rapidly switch the protonation state of the brush in PBS pH 7.4, containing 5 mM hydrogen peroxide, by application of alternating potentials +0.6 V and +0.2 V (FIG. 19), at +0.6 V hydrogen peroxide is oxidized producing protons at the interface (reverse direction of chemical Eq. (2)).

Figure 20:
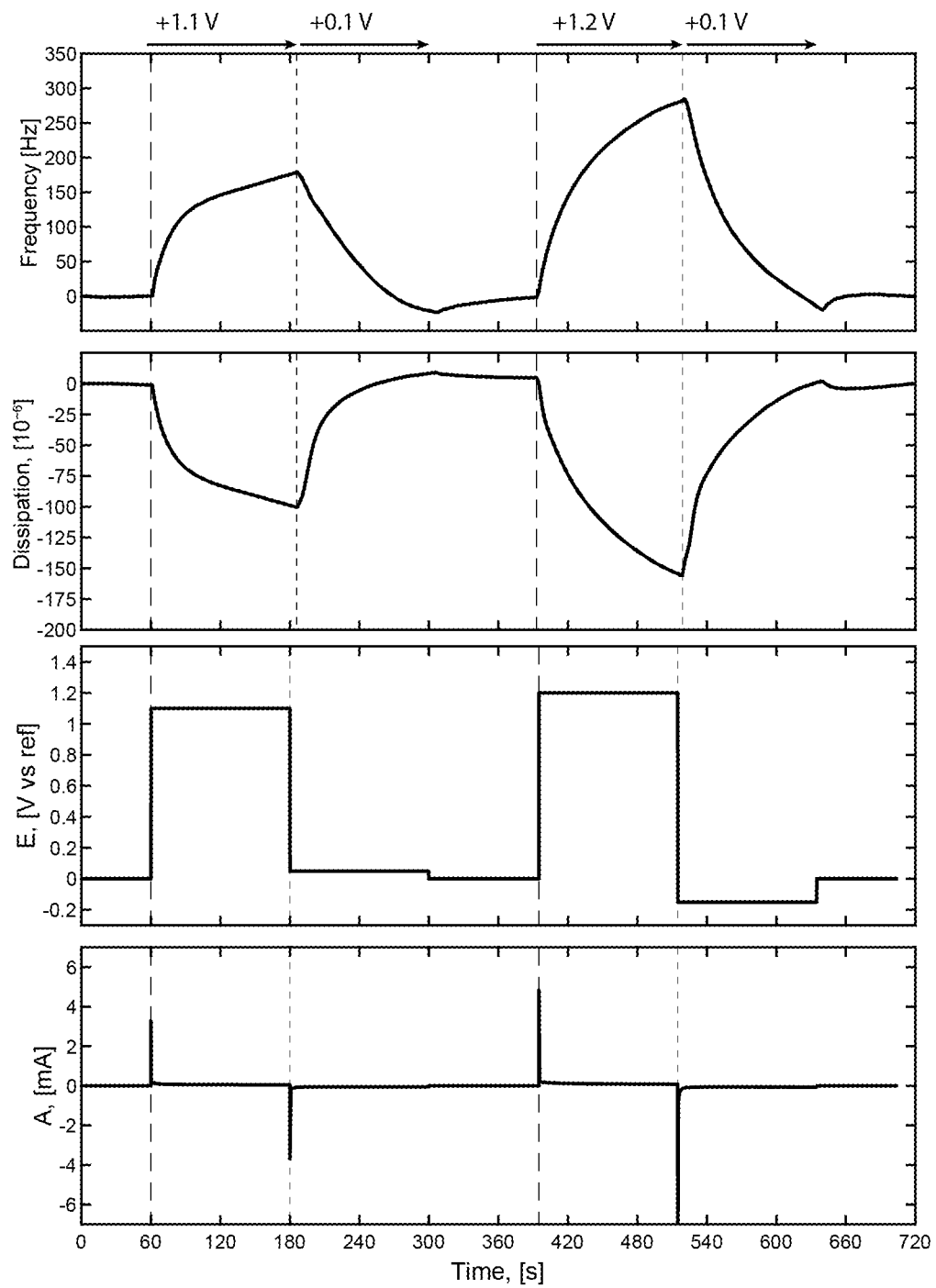
FIG. 20 shows an in-situ electrochemical QCM experiment of a polyelectrolyte brush synthesized on a platinum surface, that is covalently functionalized with GOX enzymes. The brush switches reversibly in phosphate buffered saline solution containing 10 mM glucose, when a positive potential (+1.0 V and +1.2 V) is applied.

Platinum and hydrogen peroxide for generating pH gradients allows for an extension of substrates beyond redox active molecules. Biocatalytic transformations readily produce highly redox active reaction products from less redox active substrates. For instance, GOX consumes glucose to produce hydrogen peroxide. Thus, by conjugation of GOX to a PMAA brush synthesized on a platinum surface, PMAA brushes were switched in undiluted PBS and a 10 mM glucose solution (FIG. 20). Thus, GOX conjugation to platinum PMAA brush electrodes allows for electrochemical brush switching in highly buffered solutions that contains a physiologically relevant concentration millimolar concentrations of glucose, strongly suggesting an electrochemically operated polyelectrolyte brush surfaces that can operate in biologically relevant fluids.

Figure 4:
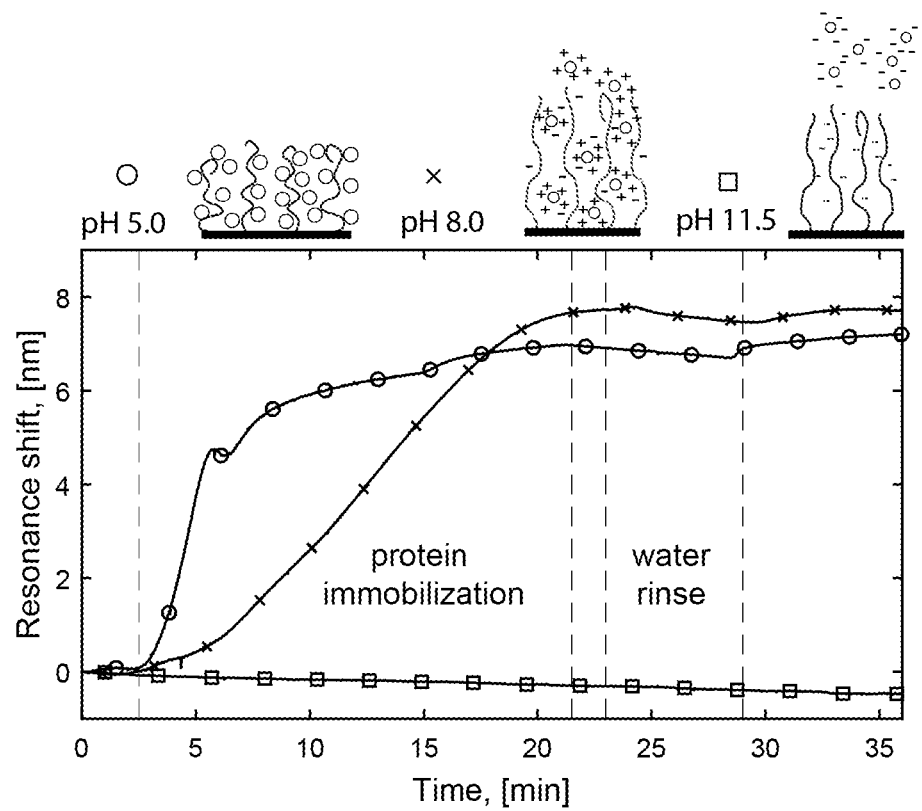
FIG. 4 shows monitoring avidin protein immobilization by hydrogen-bond interactions (circles) to a neutral PMAA brush at pH 5, and to a charged PMAA brush at pH 8 by electrostatic attraction (crosses), followed by complete absence of protein binding due to electrostatic repulsion at pH 11.5 (squares) (pI of avidin is 10) of the interface electrochemical catch-release system according to the present invention, using plasmonic nanohole arrays (response is linear to coverage).

Generic High-Capacity Protein Immobilization with an Electrochemical Catch-Release System, According to the Present Invention—Protein Immobilization and Stability in Biological Solutions Next, we describe our new method for generic high-capacity protein immobilization, which is based on keeping the polyacids, of the electrochemical catch-release system according to the present invention, in their neutral state. When the brushes are in the neutral state, at a pH below the brush $pK_a$, there is no electrostatic repulsion between the brush and protein which enables the proteins to diffuse into the polymer brush. Furthermore there is an affinity between the neutral brush and proteins at this pH because the protonated carboxylic acid groups of the polyacids readily form hydrogen bonds with the surface groups of the proteins. We utilized the affinity between the neutral polyacids and proteins at low pH as a mechanism for protein capture. Polyelectrolyte brushes are normally used for binding proteins by conjugation chemistry (R. Dong, S. Krishnan, B. A. Baird, M. Lindau, C. K. Ober, Patterned biofunctional poly(acrylic acid) brushes on silicon surfaces, Biomacromolecules 8, 3082-3092 (2007).) which prevents release in a convenient manner. Alternatively, electrostatic interactions have been used, but to be efficient this requires low ionic strength and/or a large difference between isoelectric point (pI) and $pK_a$ (J. H. Dai et al., High-capacity binding of proteins by poly(acrylic acid) brushes and their derivatives. Langmuir 22, 4274-4281 (2006); and A. Kusumo et al., High capacity, charge-selective protein uptake by polyelectrolyte brushes. Langmuir 23, 4448-4454 (2007)). We evaluated the affinity between brushes, of the electrochemical catch-release system according to the present invention, and proteins using various surface sensitive techniques at different pH, while maintaining physiological ionic strength. FIG. 4 shows an example of label-free nanoplasmonic detection (A. B. Dahlin, Sensing applications based on plasmonic nanopores: The hole story. Analyst 140, 4748-4759 (2015)) of a highly positively charged protein (avidin, pI 10) binding to PMAA brushes, i.e. the electrochemical catch-release system according to the present invention. At pH 8, the electrostatic interactions do provide high binding (3000 ng/cm²). However, at pH 5, where the brush is ~90% protonated, binding is faster and reaches the same response. For proteins with more regular pI values (~7), such as IgG antibodies, there was no detectable binding to PMAA even at pH 6.5. Yet at pH 5 binding remained very high (~4000 ng/cm²). This trend was consistent: at pH 5 we observed high binding capacity for all proteins, while in the pH range 6-8 binding was only efficient for proteins with high pI. Furthermore, when pH was higher than pI (and $pK_a$) we never detected any protein binding and bound protein were desorbed. PAA brushes behaved similarly but required lower pH to exhibit the generic high-capacity binding. (Only results for PMAA are presented from here on.)

Figure 5:
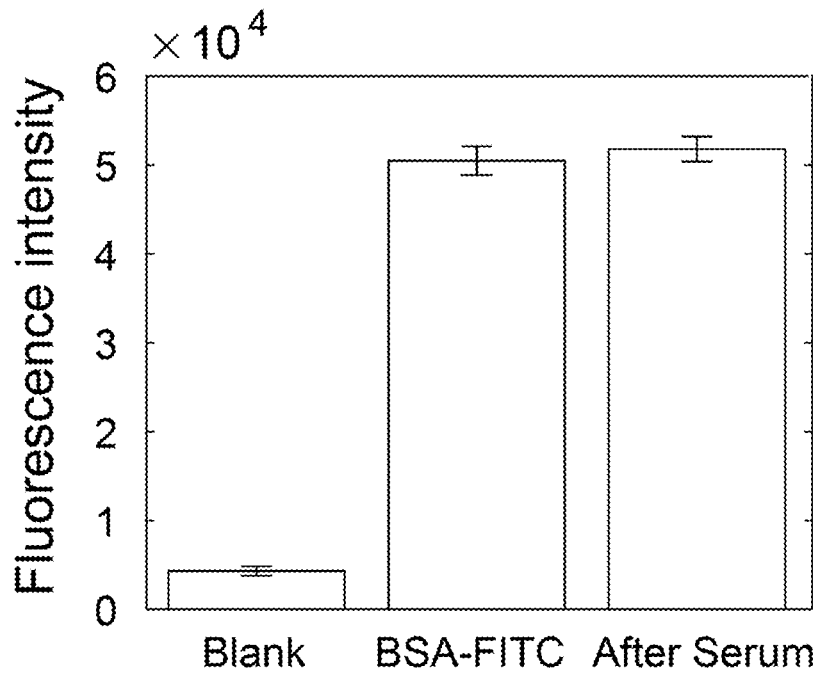
FIG. 5 shows fluorescence intensity from immobilized BSA before and after exposure to serum.

We attribute the high protein binding capacity at pH 5, i.e. of the electrochemical catch-release system according to the present invention, to hydrogen bonds between carboxylic acid donors and various acceptors on the proteins, in analogy with intermolecular complex formation between polyacids and hydrophilic polymers (Y. Osada, M. Sato, Thermal equilibrium of intermacromolecular complexes of polycarboxylic acids realized by cooperative hydrogen-bonding. Journal of Polymer Science Part C—Polymer Letters 14, 129-134 (1976); and K. L. Smith, A. E. Winslow, D. E. Petersen, Association reactions for Poly(alkylene oxides) and polymeric poly(carboxylic acids). Ind Eng Chem 51, 1361-1364 (1959)). Note that at pH 5 the secondary structure of proteins is generally considered to be preserved or at least not irreversibly altered. All proteins were irreversibly immobilized and thus the protein concentration during immobilization only influenced the loading rate, not the final amount. Furthermore, the proteins remained bound after washing with water and even after exposure to physiological fluids. FIG. 5 shows fluorescence from labelled BSA in PMAA brushes, i.e. in the electrochemical catch-release system according to the present invention, before and after exposure to complete serum set to pH 5, showing no reduction in intensity. This also confirms that immobilized proteins cannot be replaced by other proteins, although additional serum proteins also become immobilized if the brush has not reached its full loading capacity.

We emphasize that our method is the opposite of the conventional way to use polyelectrolyte brushes for protein immobilization: Here the polymers provide repulsion in their charged state (when pH>pI). Our results may seem to contradict previous studies where proteins bind to charged polymers, even when carrying the same net charge, for instance due to local "patches" on the surface (X. Xu, S. Angioletti-Uberti, Y. Lu, J. Dzubiella, M. Ballauff, Interaction of proteins with polyelectrolytes: a comparison between theory and experiment. Langmuir, (2018); and A. B. Kayitmazer, D. Seeman, B. B. Minsky, P. L. Dubin, Y. Xu, Protein-polyelectrolyte interactions. Soft Matter 9, 2553-2583 (2013)). This is to a large extent explained by the fact that all our measurements were performed at physiological ionic strength where screening eliminates electrostatic attraction. Furthermore, a highly hydrophilic brush like PMAA in its charged state (~90% water, is expected to repel proteins also due to conformational entropy loss and osmotic pressure (G. Ferrand-Drake del Castillo, G. Emilsson, A. Dahlin, Quantitative analysis of thickness and pH actuation of weak polyelectrolyte brushes. J Phys Chem C 122, 27516-27527 (2018)).

Figure 6:
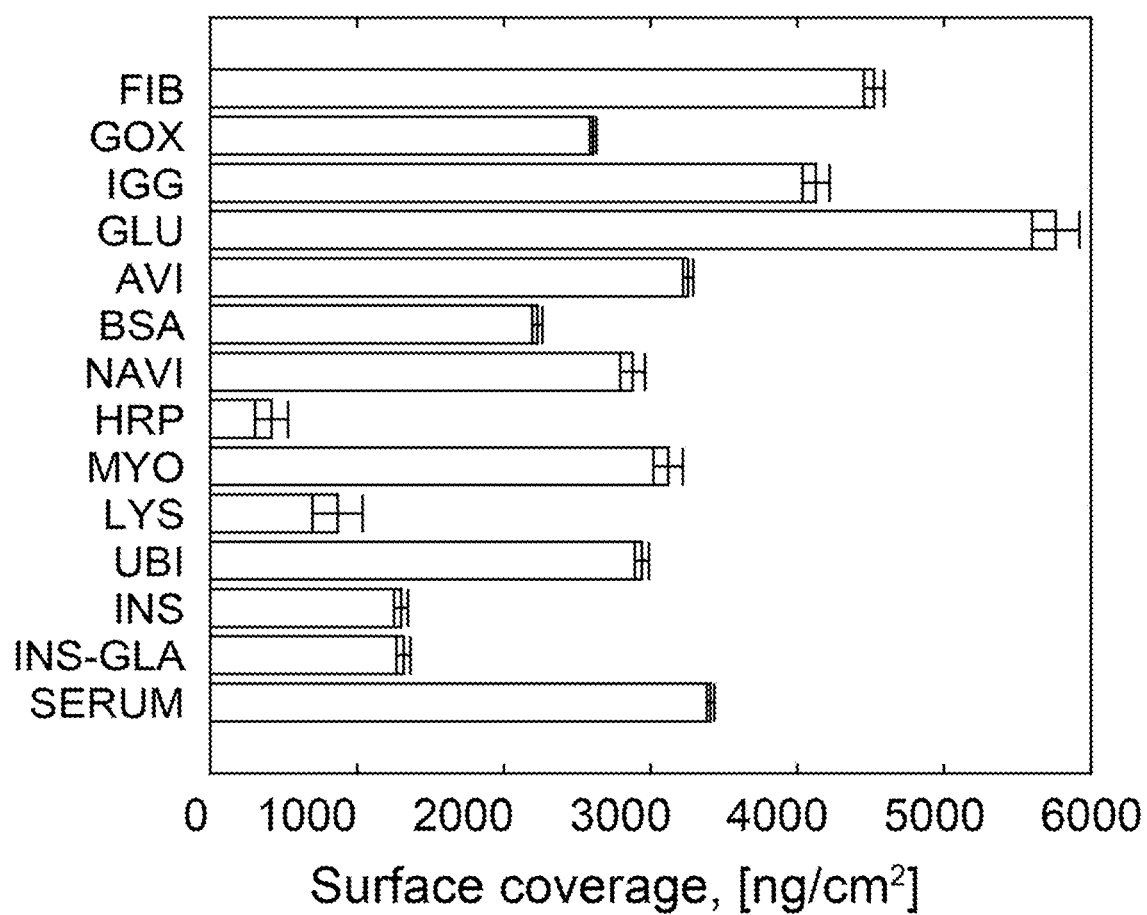
FIG. 6 shows quantification of surface coverage of different proteins (FIB: Fibrinogen, GOX: glucose oxidase, IGG: immuoglobulin, GLU: Glucosidase, AVI: avidin, BSA: bovine serum albumin, NAVI: Neutravidin, HRP: horse radish peroxidase, MYO: myoglobulin, LYS: Lysozyme, UBI: ubiquitin, INS: insulin, INS-GLA: insulin-glargine, SERUM: 10× diluted and filtered serum).

The immobilized protein amount was quantified by fitting Fresnel models to SPR spectra recorded in the dry state (FIG. 5). This method gives high accuracy since the protein refractivity is very similar to that of the polymers (G. Ferrand-Drake del Castillo et al., Enzyme immobilization in polyelectrolyte brushes: High loading and enhanced activity compared to monolayers. Langmuir 35, 3479-3489 (2019)). A wide range of proteins with different molecular weight (M) and pI were tested, resulting in high surface coverage in all cases (FIG. 6). When normalizing to the coverage of PMAA, the protein amount correlated with M (p<0.05) but not pI, confirming that the binding is not due to electrostatic attraction. The trend of higher surface coverage with higher M can be understood from a simple scaling argument: Given that the polymers interact with the surface of a protein with size R, the amount of polymer in contact with the protein is proportional to $R^2$, while M is proportional to $R^3$. Hence the mass of immobilized protein per mass of available polymer should scale with $M^{1/3}$, in reasonable agreement with our results. The remaining variation can be attributed to different degrees of good hydrogen bond acceptor groups on the surfaces of the proteins. The results strongly suggest that the polymers are "wrapping around" the hydrophilic protein exterior. Note that even the lowest immobilized amount, horseradish peroxidase at 417 ng/cm$^2$, still corresponds to more than a monolayer. In addition, the brushes, i.e. polyelectrolyte arrangement of the present invention, can be made thicker to store even more proteins. In this work we kept the hydrated thickness comparable to the evanescent field in SPR to enable height probing (G. Ferrand-Drake del Castillo, G. Emilsson, A. Dahlin, Quantitative analysis of thickness and pH actuation of weak polyelectrolyte brushes. J Phys Chem C 122, 27516-27527 (2018)). Protein immobilization led to a compression of the brush as expected from multivalent interactions bridging several chains (J. Yu et al., Multivalent counterions diminish the lubricity of polyelectrolyte brushes. Science 360, 1434 (2018)), thereby overcoming the entropic penalty of insertion (N. Fomina et al., An electrochemical platform for localized pH control on demand. Lab Chip 16, 2236-2244 (2016)).

The high capacity for proteins immobilization to polymer brushes suggests that it could be used in protein purification applications (Jain P, Baker G L, Bruening M L. Applications of Polymer Brushes in Protein Analysis and Purification. Annu Rev Anal Chem. 2, 387-408 (2009)). In principle, the protein surface coverage of PMAA brushes on flat surfaces (FIG. 6) should translate to equal surface coverage to polymer brushes within a porous solid support instead as that of a flat surface. The corresponding protein binding per volume of porous solid support functionalized with polyelectrolyte brushes can potentially become very high. We tested this by polymerization of PMAA brushes within a reticulated glassy (vitreous) carbon electrode solid support, with minor adaptions of the synthesis protocol used for flat surfaces. A weight increase by 140 mg/cm$^3$ of the dry electrode support indicated successful polymerization within the entire internal surface of the electrode. The BSA protein uptake of the PMAA functionalized electrode at pH 5 was determined to be 50 mg/cm$^3$ (static binding capacity). However, is highly likely that the binding capacity can increase even further by optimization of (1) the polymer brush synthesis within high internal surface area materials and (2) maximizing the porosity and available surface area for polymerization. In our preliminary tests, we used a porous scaffold with a very high internal porosity (96.5%), this is advantageous if used in flow applications, which is the case in most commercial protein purification equipment, since it dramatically lowers the pressure drop and increases mass transport throughout the electrode. However, high internal porosity lowers the internal surface area. The tradeoff between porosity and surface area can most likely be substantially pushed towards high porosity with optimization of the polymer brush synthesis within the scaffold, because of the very high protein immobilization capacity per surface area displayed by the polymer brushes (by at least a factor 100 compared to conventional surfaces). In a previous study of the protein binding capacity of a porous alumina membranes functionalized with poly(hydroxyl ethyl) acrylate (PHEA) polymer brushes showed that a protein binding capacity of 150 mg/cm$^3$ (Sun L, Dai J, Baker G L, Bruening M L. High-capacity, protein-binding membranes based on polymer brushes grown in porous substrates. Chem Mater.

Figure 16:
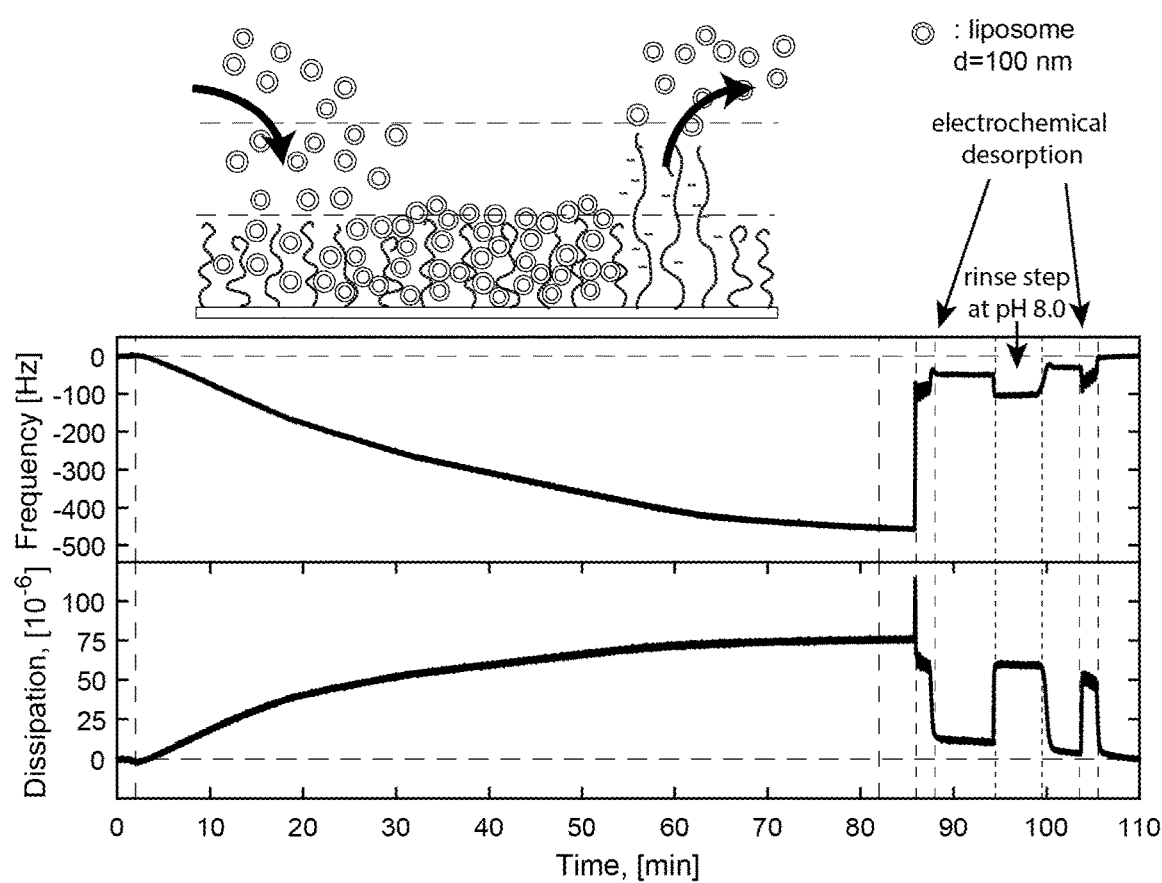
FIG. 16. Liposome interaction with PMAA at pH 5 monitored by QCM which shows high loading several multilayers of liposomes followed by electrochemical release by the electrochemical catch-release system according to the present invention.

18, 4033-4039 (2006)), a capacity for protein immobilization that should be attainable, but in no way pose a limitation, to the capacity for our a porous electrode support of our electrochemical protein catch and release system. In summary, our method could be utilized for protein purification with a binding capacity in the same range as conventional chromatography (Gagnon P. Technology trends in antibody purification. J Chromatogr A. 1221, 57-70. (2012)), while offering electrochemically induced binding and elution combined with a advantageous flow through properties, high mass transfer rates and minimal pressure drop. A few other compounds could also be bound in high amounts to PMAA at pH 5. One important example is poly(ethylene glycol) (PEG) and PEG-modified compounds. PEG-modification of a protein did not result in its exclusion from the brush. Instead, we observed binding of an amount comparable to that of the same protein in its native state. This is expected due to hydrogen bonds with the ether oxygen in PEG (Y. Osada, M. Sato, Thermal equilibrium of intermacromolecular complexes of polycarboxylic acids realized by cooperative hydrogen-bonding. Journal of Polymer Science Part C—Polymer Letters 14, 129-134 (1976)). Furthermore, liposomes could be bound in multilayers (FIG. 16) without the need for tethers (C. M. Agrawal, K. A. Athanasiou, Technique to control pH in vicinity of biodegrading PLA-PGA implants. J Biomed Mater Res 38, 105-114 (1997)).

These results suggest high potential for applications in drug delivery where PEG-modified compounds and liposomal carriers are common. At the same time, no binding was detected at all for other biomacromolecules such as polysaccharides (e.g. hyaluronic acid), ribonucleic acids (e.g. double stranded DNA) or short peptides (e.g. oxytocin). Thus, the PMAA brush is very specific to proteins and a few other types of macromolecules.

Figure 9:
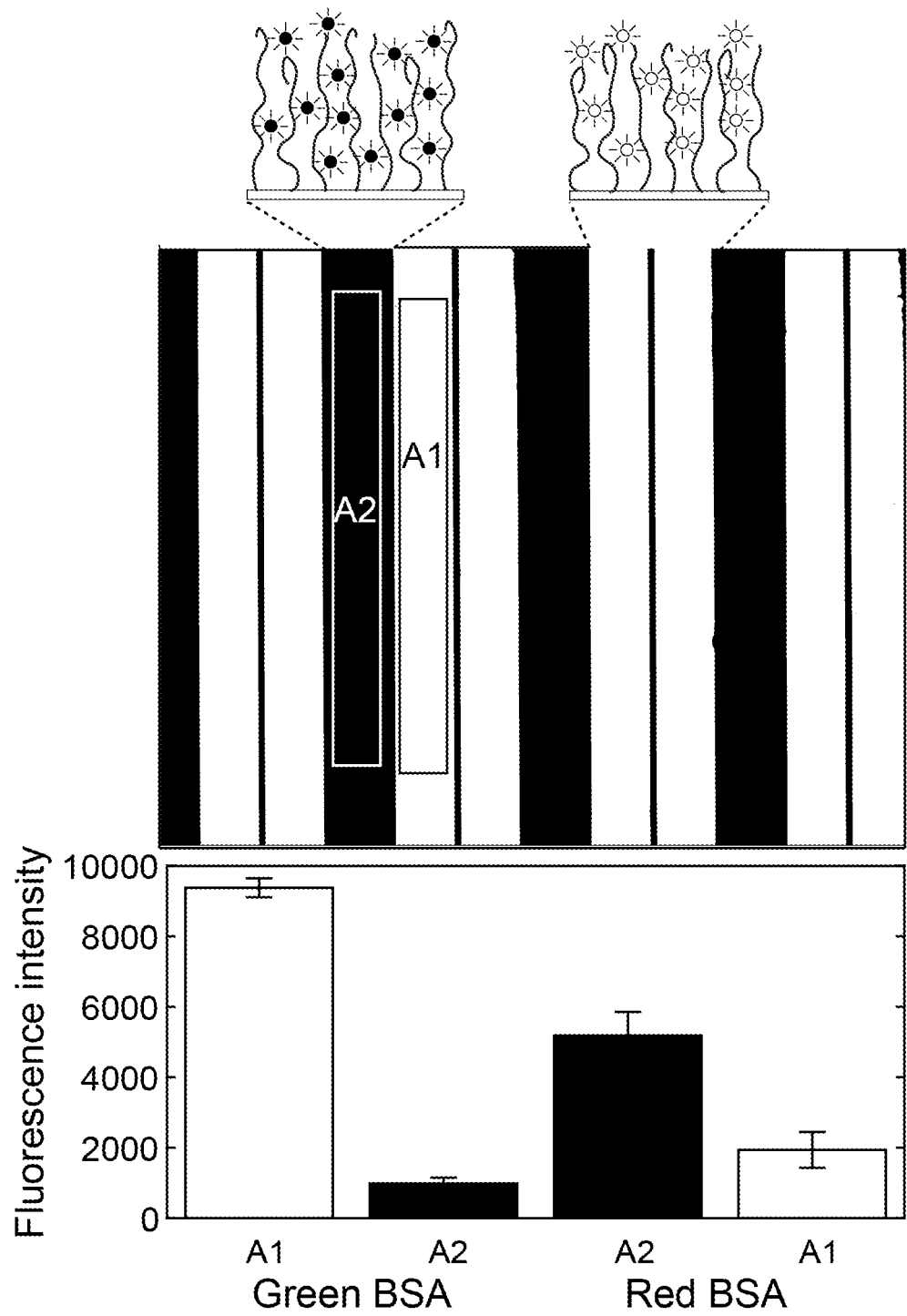
FIG. 9 shows fluorescence of proteins immobilized to interdigitated microelectrode stripes where patterning is accomplished by local release of green (white electrodes) proteins from one electrode followed by the addition of a red (black electrodes) protein to the empty polymer brush electrode by a second immobilization step.

Desorption of protein from the brush occurs when the pH of the brush increases. The mechanism behind the desorption is the reverse of what happens during protein capture. When the pH increases within the protein loaded brush, the carboxylic acids of the polyelectrolyte brush are deprotonated breaking the bond between the brush and the protein. Furthermore the brush becomes negatively charged as the pH shifts above the $pK_a$ of the brush, similarly when the pH is above the isoelectric point the proteins become net negatively charged, triggering electrostatic repulsion between the protein and the brush. The possibility to electrochemically switch the brush (FIG. 3) together with the fact that proteins desorb at sufficiently high pH suggests that controlled release is possible. We confirmed this first by applying repeated voltammetry sweeps in QCM (FIG. 7), showing that the signal gradually returned to the baseline (before immobilization). SPR spectra showed the same behavior (FIG. 8*b*) and that the capture-release was possible to reproduce on the same surface with no detectable change in storage capacity or release efficiency (tested up to 10 cycles). We also observed that for proteins with high pI, the negative potential had to be applied for a longer time to raise the pH sufficiently, but all proteins tested could be fully released. Further, we used microelectrodes with plasmonic nanohole arrays to demonstrate localized release and patterning. Here we refer also to A. B. Dahlin et al., High-resolution microspectroscopy of plasmonic nanostructures for miniaturized biosensing. Analytical Chemistry 81, 6572-6580 (2009). FIG. 9 shows patterning of proteins on different microelectrodes by selective release and subsequent immobilization.

Figure 10:
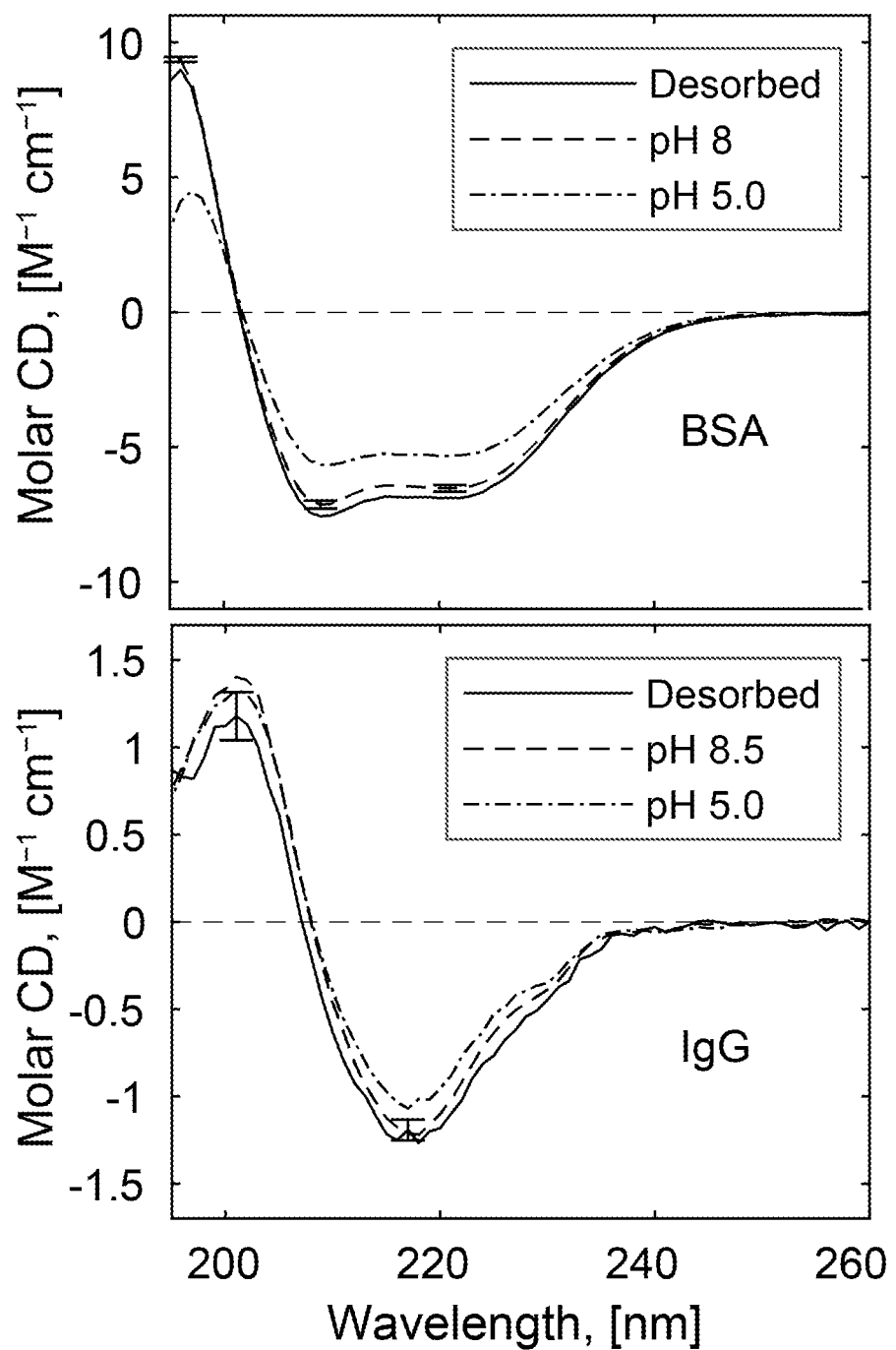
FIG. 10 shows circular dichroism spectra of BSA and IGG before immobilization and after release.
Figure 11:
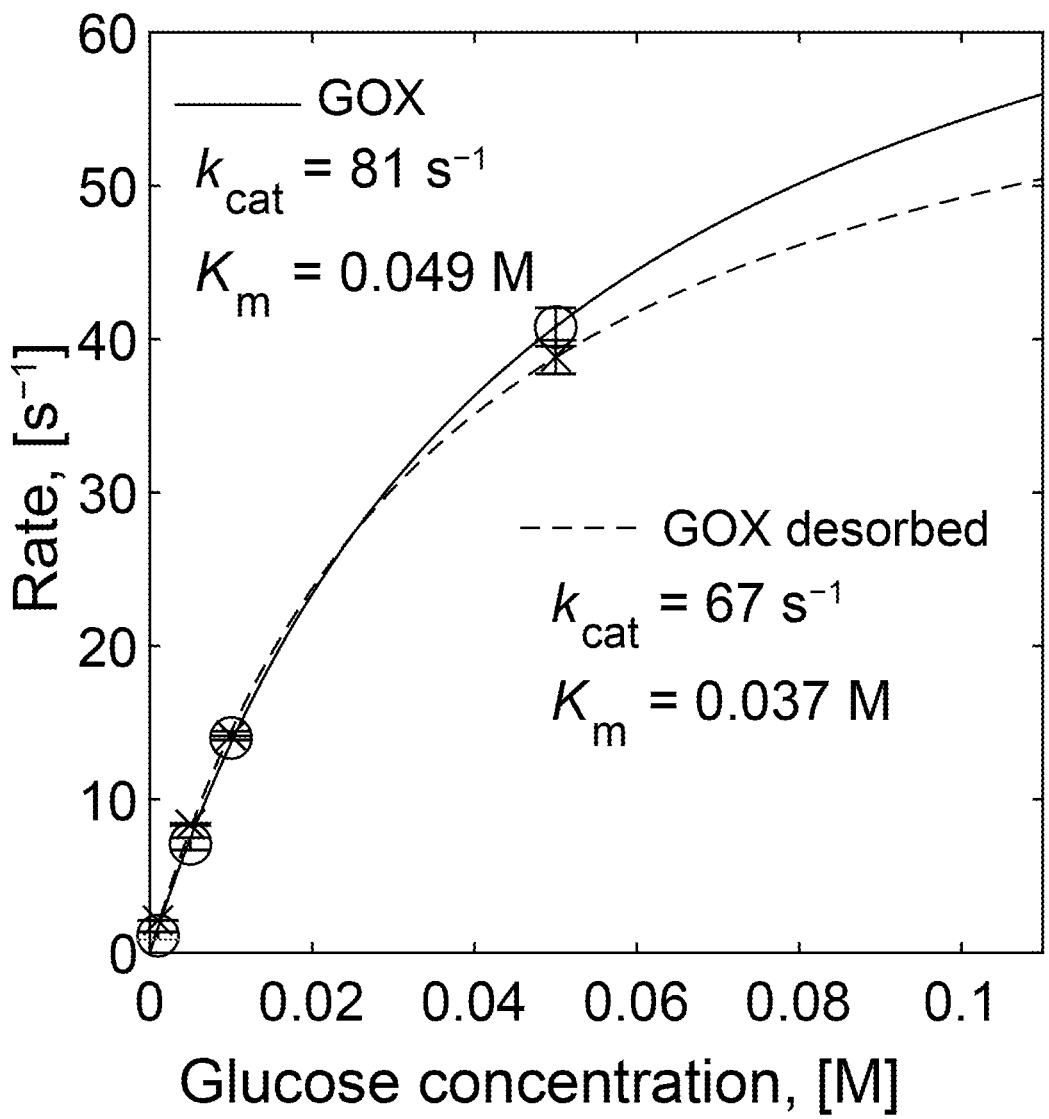
FIG. 11 shows Michaelis-Menten analysis of GOX activity before immobilization and after release.
Figure 17:
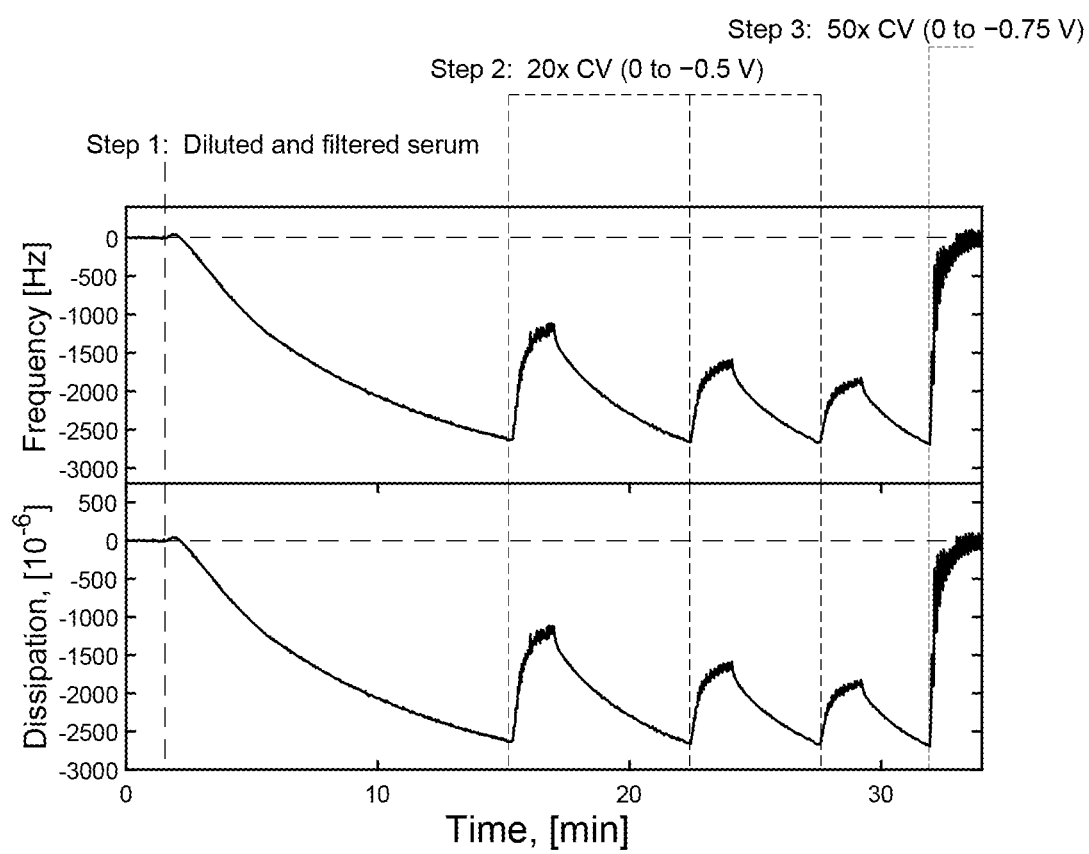
FIG. 17 shows an in-situ electrochemical QCM measurement where serum (10× diluted with water and filtered, pH 7.4) is exposed to the electrochemical catch-release system resulting in spontaneous immobilization of serum protein (Step 1). Twenty repeating CV scans with a potential window between 0 V and −0.5 V were applied at 15 min, 22 min, and 27 min into the experiment, resulting in partial protein release (Step 2). Fifty repeated CV scans with a larger potential window 0 V to −0.75 V was applied resulting in complete protein release from the electrochemical catch-release system.

In order to test that the higher order structure of the proteins was preserved after capture and release, we performed circular dichroism on BSA and IgG, showing no detectable change in secondary structure (FIG. 10). In addition, Michaelis-Menten analysis of GOX activity assays illustrated very small changes in enzyme activity after immobilization and desorption (FIG. 11). We consider the preserved bioactivity quite remarkable since many immobilization methods, in particular hydrophobic interactions (J. N. Talbert, J. M. Goddard, Enzymes on material surfaces. Colloids and Surfaces B: Biointerfaces 93, 8-19 (2012)), lead to unfolding of proteins and loss of bioactivity. We attribute the maintained secondary structure to the hydrogen bond interactions with the exterior surface of the proteins rather than the interior, in agreement with the molecular weight dependence. The total salt concentration of the solution strongly influences the brush $pK_a$ (Ferrand-Drake del Castillo G, Hailes R L N, Dahlin A. Large Changes in Protonation of Weak Polyelectrolyte Brushes with Salt Concentration—Implications for Protein Immobilization. J Phys Chem Lett. 11(13):5212-8 (2020)). Specifically, the $pK_a$ shifts to higher values at a lower salt concentration, thus promoting protein binding to the brush at higher pH values. For serum diluted by water, rather than PBS, we noted a very high quantity of spontaneous protein immobilization even at pH 7.4 (Step 1 FIG. 17). In addition we could obtain charge selective separation, i.e. isoelectric point separation, of proteins based on the relative electrostatic repulsion of proteins to the brush depending on the applied electrochemical potential. By application of continuous cyclic voltammetry scans within a small potential window (−0.5 V to 0 V) during serum exposure (Step 2 FIG. 17), a fraction of proteins with low pI release from the brush due to electrostatic repulsion to the brush. However, the fraction of high pI proteins remain bound to the brush due to lack of electrostatic repulsion. Upon release of the electrochemical signal, new proteins bound to the now partially empty brush, thus refilling the unoccupied void volume of the brush due to the low pI fraction. By repeating this cycle the brush is effectively accumulating proteins with high pI out of the serum solution of protein, giving rise to a isoelectric point-based separation of proteins. By changing the CV scan window to a higher value (Step 3 FIG. 17), all of the bound protein was released from the brush emphasizing that the high pI protein can still be removed at any time by charging the brush electrochemically to a sufficient extent. This electrochemical activation of the polymer brush for capture of proteins on demand out of serum could prove useful in protein handling in bioanalytical applications. The average power consumption of the system while scanning the surface between (~0.5 V to 0 V) was 9 $\mu W/cm^2$, The reason for extremely low power consumption is that the only power required is that which generates a nanoscale chemical pH gradient. The power consumption is compatible with state of the art biocatalytic biofuel cells and implant technology with low power demands (Song Y, Min J, Gao W. Wearable and Implantable Electronics: Moving toward Precision Therapy. ACS Nano. 13, 12280-12286, (2019)).

Figure 18:
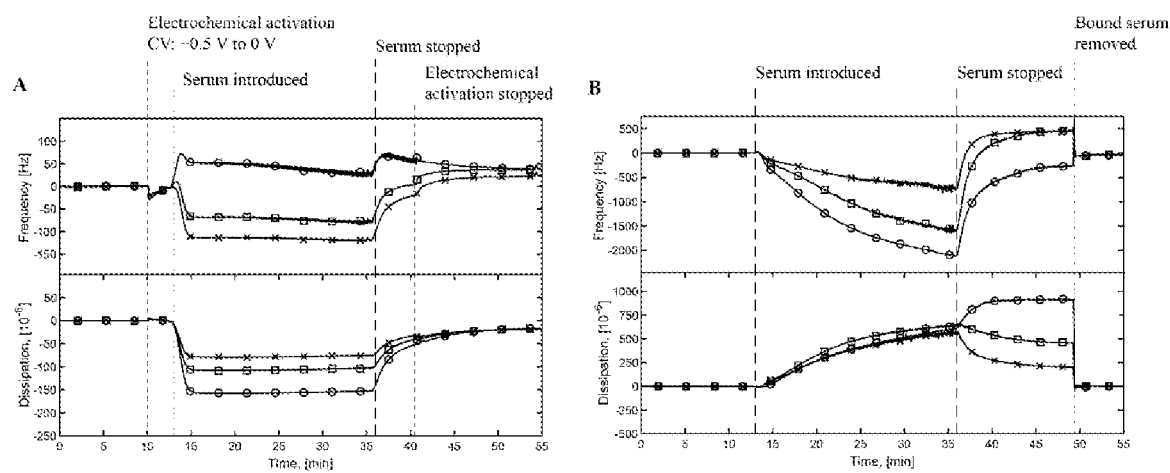
FIG. 18 shows in-situ electrochemical QCM experiments where diluted serum is introduced to PMAA brushes synthesized on a platinum surface where in (A) electrochemical activation of the surface (continuous CV scans) results in a highly non-fouling state of the surface, compared to in (B) without electrochemical activation, however complete desorption of bound proteins is still accomplished when a sufficiently large potential is applied.

In diluted serum solutions pH 7.4 we noted that polymer brushes in combination with continuous cyclic voltammetry scans that maintain a local high pH acts to produce a highly protein and biomolecule repellant surface. When a PMAA brush on platinum surface was continuously scanned with CV scans between −0.5 V to 0 V the brush completely resisted protein binding (FIG. 18. A). In comparison, without electrochemical activation prior to exposure to the serum (FIG. 18 B), very large quantities of protein immobilized to the brush (thousands of Hertz and substantial dissipation change). However, complete desorption of bound proteins of the was accomplished by application of twenty CV scans within the same potential range (−0.5 V to 0 V) as used in (FIG. 18A).

Figure 7:
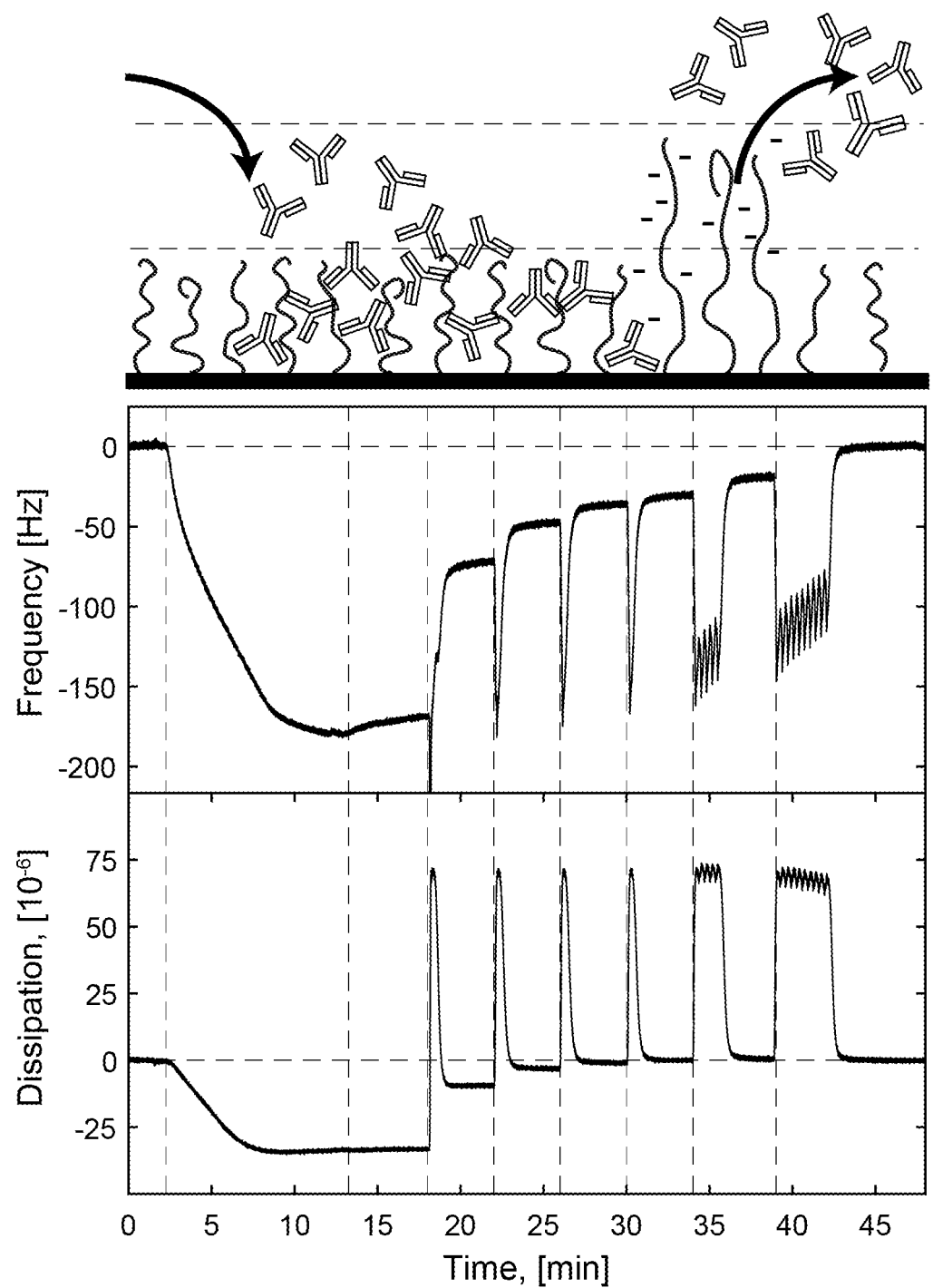
FIG. 7 shows electrochemical QCM showing stepwise release of IGG in real-time.
Figure 13:
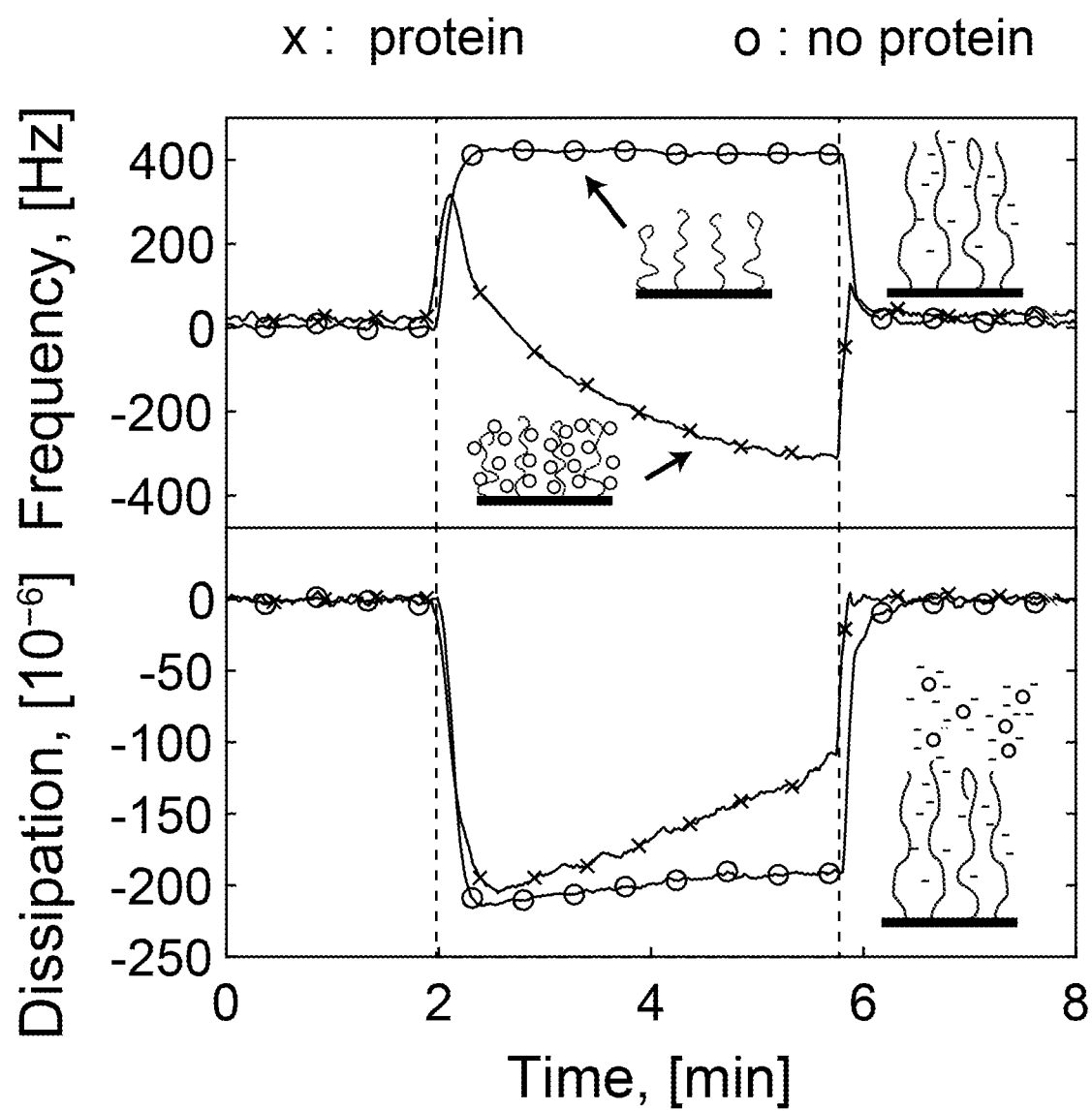
FIG. 13 shows by in-situ electrochemical QCM protein "adsorption on demand" by applying +0.5 V in PBS with 5 mM hydroquinone.

So far we have shown on-demand release or the prevention of protein binding of protein by locally increasing the pH at the electrode (FIG. 7). But since we can also locally decrease the pH at the electrode (FIG. 12), and essentially set any pH at the electrode surface, this allows for electrochemically activated capture and release from a buffered solution of proteins at any solution pH. For instance, in the presence of hydroquinone 5 mM we were able to bind protein to the polyelectrolyte brush when a constant electrochemical potential +0.5 V was applied (FIG. 13). Despite using in undiluted PBS (pH 7.4), a positive potential made it possible to induce protein binding as efficiently as at pH 5. In principle, an electrochemical catch and release system that consists of a platinum electrode support in combination with functionalization of GOX, can utilize natural concentrations of glucose instead of hydroquinone to switch the brush. Thus, the electrochemical catch and release system could operate to capture or release proteins on-demand in biological environments without any additional supplements.

Conclusion

In conclusion, we have shown a new type of high-capacity protein immobilization in polyacidic brushes, i.e. polyelectrolyte arrangement of the present invention, and subsequent release by electrochemical control of interfacial pH, i.e. the electrochemical catch-release system, in accordance with the present invention. The proteins remain bound in physiological fluids and their structure is preserved. It is also possible to switch a surface from repelling to protein binding. The key to successful electrochemical switching lies in the chemistry used to graft the polymers to the surface. In this work gold, platinum and carbon electrode surfaces were modified, but the method is applicable to any surface that can bind the diazonium salt (J. Pinson, F. Podvorica, Attachment of organic layers to conductive or semiconductive surfaces by reduction of diazonium salts. Chemical Society Reviews 34, 429-439 (2005)). Similarly, we demonstrated that the storage capacity of the electrochemical capture and release system can match current commercial protein purification materials, and can likely be improved even further by consideration of other structures with higher effective area. We predict several application areas for this technology. Implementation should be straightforward in separation technologies and analytical devices where proteins are in focus. In the long-term we envision utilizing the technology described herein, i.e. the electrochemical catch-release system, for controlled release of proteins such as therapeutic antibodies from implanted devices.

What is claimed is:

1. An electrochemical catch-release system for repeated use comprising:
    pH-responsive polymers, wherein (i) the polymers respond to pH changes by switching between a neutral and a charged state, and (ii) the polymers are covalently linked to a conductive structure via a monolayer of aryl bonds formed by chemical reduction of an aryl diazonium salt, forming a polyelectrolyte arrangement,
    the polyelectrolyte arrangement being arranged to,
        when the covalently bound polymers are in a neutral state, catch an entity, wherein the entity is a protein, a vesicle, a compound modified with poly(ethylene glycol), or a drug, and
        when the polymers are in a charged state, release by electrostatic repulsion an entity captured by the polyelectrolyte arrangement, and
    a device for applying an electrochemical potential to the polyelectrolyte arrangement, thereby generating a pH change to induce a switch of the polyelectrolyte arrangement from the neutral state to the charged state or the reverse in the presence of redox active species.

2. The electrochemical catch-release system according to claim 1, wherein the pH-responsive polymer is a polyacidic polymer comprising a carboxylic acid group.

3. The electrochemical catch-release system of claim 1, wherein the conductive structure is a planar surface, an electrode surface, a porous material, or a nanohole array.

4. The electrochemical catch-release system of claim 1, wherein the conductive structure comprises or is made of carbon, a noble metal, a conducting oxide, stainless steel or a conducting polymer.

5. The electrochemical catch-release system of claim 1, wherein the polyelectrolyte arrangement comprises a polyelectrolyte brush, film, gel or layer.

6. The electrochemical catch-release system of claim 1, wherein the system is miniaturized such that dimensions of the system is nanoscale, microscale or mesoscale in size.

7. The electrochemical catch-release system of claim 1, wherein the redox active species used to induce a switch in the polyelectrolyte arrangement from the charged state of the polymers to a neutral state, is selected from hydroquinone, hydrogen peroxide, dopamine hydrochloride (DOPA), ascorbic acid, 4-aminophenethyl alcohol, tyrosol, 3,4-dihydroxyphenylacetic acid (DOPAC), β-nicotinamide adenine dinucleotide (β-NAD), reduced β-NAD (β-NADH) disodium salt hydrate, and oxygen.

8. The electrochemical catch-release system of claim 1, further comprising enzymes bound to the polyelectrolyte arrangement.

9. A protein capturing system comprising the electrochemical catch-release system of claim 1.

10. A drug releasing system comprising the electrochemical catch-release system of claim 1.

11. A method of catching and releasing an entity selected from the group consisting of a protein, a vesicle, a compound modified with poly)ethylene glycol), and a drug, in a catch-release system, comprising
    binding pH-responsive polymers covalently to a conductive structure via a monolayer of aryl bonds formed by chemical reduction of an aryl diazonium salt, forming a polyelectrolyte arrangement,
    bringing a solution comprising said entity in contact with the polyelectrolyte arrangement when the covalently bound polymers are in a neutral state, allowing the polyelectrolyte arrangement to catch said entity by non-electrostatic interactions, and
    applying an electrochemical potential to the polyelectrolyte arrangement in the presence of redox active species to induce a switch in the polyelectrolyte arrangement from the neutral state of the polymers to a charged state of the polymers, thereby releasing the entity from the polyelectrolyte arrangement by electrostatic repulsion.

12. The method of claim 11, further comprising applying an electrochemical potential to the polyelectrolyte arrangement in the presence of redox active species, to induce a switch in the polyelectrolyte arrangement from the charged state of the polymers to a neutral state of the polymers, thereby allowing the polyelectrolyte arrangement to catch an entity by non-electrostatic interactions.

\* \* \* \* \*